(12) United States Patent
Say et al.

(10) Patent No.: US 6,654,625 B1
(45) Date of Patent: Nov. 25, 2003

(54) MASS TRANSPORT LIMITED IN VIVO ANALYTE SENSOR

(75) Inventors: James L. Say, Alameda, CA (US); Henning Sakslund, Pleasant Hill, CA (US); Michael F. Tomasco, Danville, CA (US); Jay D. Audett, Mountain View, CA (US); Hyun Cho, Berkeley, CA (US); Duane O. Yamasaki, El Cerrito, CA (US); Adam Heller, Austin, TX (US)

(73) Assignee: TheraSense, Inc., Alameda, CA (US)

( * ) Notice: Subject to any disclaimer, the term of this patent is extended or adjusted under 35 U.S.C. 154(b) by 0 days.

(21) Appl. No.: 09/595,708

(22) Filed: Jun. 16, 2000

Related U.S. Application Data
(60) Provisional application No. 60/194,618, filed on Apr. 5, 2000, and provisional application No. 60/139,936, filed on Jun. 18, 1999.

(51) Int. Cl.$^7$ ................................................ A61B 5/05
(52) U.S. Cl. ..................... 600/347; 600/345; 600/365
(58) Field of Search ................................ 600/345, 347, 600/348, 365; 204/403, 403.01, 403.04–403.07, 403.09–403.14

(56) References Cited

U.S. PATENT DOCUMENTS

| | | |
|---|---|---|
| 3,260,656 A | 7/1966 | Ross, Jr. |
| 3,653,841 A | 4/1972 | Klein |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,151,845 A | 5/1979 | Clemens |
| 4,168,205 A | 9/1979 | Danninger et al. |

(List continued on next page.)

FOREIGN PATENT DOCUMENTS

| | | |
|---|---|---|
| DE | 29 03 216 | 8/1979 |
| DE | 227 029 A3 | 9/1985 |
| EP | 0 048 090 A2 | 3/1982 |

(List continued on next page.)

OTHER PUBLICATIONS

Abruña, H. D. et al., "Rectifying Interfaces Using Two–Layer Films of Electrochemically Polymerized Vinylpyridine and Vinylbipyridine Complexes of Ruthenium and Iron on Electrodes," *J. Am. Chem. Soc.*, 103(1):1–5 (Jan. 14, 1981).

Albery, W. J. et al., "Amperometric enzyme electrodes. Part II. Conducting salts as electrode materials for the oxidation of glucose oxidase," *J. Electroanal. Chem. Interfacial Electrochem.*, 194(2) (1 page—Abstract only) (1985).

(List continued on next page.)

*Primary Examiner*—Robert L. Nasser
*Assistant Examiner*—Patricia Mallari
(74) *Attorney, Agent, or Firm*—Merchant & Gould P.C.

(57) ABSTRACT

An in vivo electrochemical sensor including a working electrode, and an analyte-responsive sensing layer proximate the working electrode. The sensing layer is exposed at an edge of the sensor, wherein the sensor signal is limited, at least in part, by mass transport of analyte to the sensing layer. The sensor is configured and arranged for implantation into the body of a mammal for contact with body fluids of the mammal. The analyte diffuses to the sensing element via the edge of the sensor, thereby restricting mass transport of the analyte to the sensing element. This is because the solution-contacting surface area of the sensor edge is much smaller than an open face of the sensing layer.

25 Claims, 14 Drawing Sheets

U.S. PATENT DOCUMENTS

| | | | |
|---|---|---|---|
| 4,172,770 A | 10/1979 | Semersky et al. | |
| 4,178,916 A | 12/1979 | McNamara | |
| 4,206,755 A | 6/1980 | Klein | |
| 4,224,125 A | 9/1980 | Nakamura et al. | |
| 4,240,438 A | 12/1980 | Updike et al. | |
| 4,240,889 A | 12/1980 | Yoda et al. | |
| 4,247,297 A | 1/1981 | Berti et al. | |
| 4,271,119 A | 6/1981 | Columbus | |
| 4,318,784 A | 3/1982 | Higgins et al. | |
| 4,340,458 A | 7/1982 | Lerner et al. | |
| 4,356,074 A | 10/1982 | Johnson | |
| 4,365,637 A | 12/1982 | Johnson | |
| 4,366,033 A | 12/1982 | Richter et al. | |
| 4,375,399 A | 3/1983 | Havas et al. | |
| 4,384,586 A | 5/1983 | Christiansen | |
| 4,392,933 A | 7/1983 | Nakamura et al. | |
| 4,401,122 A | 8/1983 | Clark, Jr. | |
| 4,404,066 A | 9/1983 | Johnson | |
| 4,407,959 A | 10/1983 | Tsuji et al. | |
| 4,418,148 A | 11/1983 | Oberhardt | |
| 4,420,564 A | 12/1983 | Tsuji et al. | |
| 4,427,770 A | 1/1984 | Chen et al. | |
| 4,431,004 A | 2/1984 | Bessman et al. | |
| 4,436,094 A | 3/1984 | Cerami | |
| 4,440,175 A | 4/1984 | Wilkins | |
| 4,444,892 A | 4/1984 | Malmros | |
| 4,450,842 A | 5/1984 | Zick et al. | |
| 4,461,691 A | 7/1984 | Frank | |
| 4,469,110 A | 9/1984 | Slama | |
| 4,477,314 A | 10/1984 | Richter et al. | |
| 4,483,924 A | 11/1984 | Tsuji et al. | |
| 4,484,987 A | 11/1984 | Gough | |
| 4,522,690 A | 6/1985 | Venkatasetty | |
| 4,524,114 A | 6/1985 | Samuels et al. | |
| 4,526,661 A | 7/1985 | Steckhan et al. | |
| 4,534,356 A | 8/1985 | Papadakis | |
| 4,538,616 A | 9/1985 | Rogoff | |
| 4,543,955 A | 10/1985 | Schroeppel | |
| 4,545,382 A | 10/1985 | Higgins et al. | |
| 4,552,840 A | 11/1985 | Riffer | |
| 4,560,534 A | 12/1985 | Kung et al. | |
| 4,571,292 A | 2/1986 | Liu et al. | |
| 4,573,994 A | 3/1986 | Fischell et al. | |
| 4,581,336 A | 4/1986 | Malloy et al. | |
| 4,595,011 A | 6/1986 | Phillips | |
| 4,595,479 A | 6/1986 | Kimura et al. | |
| 4,619,754 A | 10/1986 | Niki et al. | |
| 4,633,878 A | 1/1987 | Bombardieri | |
| 4,637,403 A | 1/1987 | Garcia et al. | |
| 4,650,547 A | 3/1987 | Gough | |
| 4,654,197 A | 3/1987 | Lilja et al. | |
| 4,655,880 A | 4/1987 | Liu | |
| 4,655,885 A | 4/1987 | Hill et al. | |
| 4,671,288 A | 6/1987 | Gough | |
| 4,679,562 A | 7/1987 | Luksha | |
| 4,680,268 A | 7/1987 | Clark, Jr. | |
| 4,682,602 A | 7/1987 | Prohaska | |
| 4,684,537 A | 8/1987 | Graetzel et al. | |
| 4,685,463 A | 8/1987 | Williams | |
| 4,703,756 A | 11/1987 | Gough et al. | |
| 4,711,245 A | 12/1987 | Higgins et al. | |
| 4,717,673 A | 1/1988 | Wrighton et al. | |
| 4,721,601 A | 1/1988 | Wrighton et al. | |
| 4,726,378 A | 2/1988 | Kaplan | |
| 4,750,496 A | 6/1988 | Reinhart et al. | |
| 4,757,022 A | 7/1988 | Shults et al. | |
| 4,758,323 A | 7/1988 | Davis et al. | |
| 4,759,371 A | 7/1988 | Franetzki | |
| 4,759,828 A | 7/1988 | Young et al. | |
| 4,764,416 A | 8/1988 | Ueyama et al. | |
| 4,776,944 A | 10/1988 | Janata et al. | |
| 4,781,798 A | 11/1988 | Gough | |
| 4,784,736 A | 11/1988 | Lonsdale et al. | |
| 4,795,707 A | 1/1989 | Niiyama et al. | |
| 4,805,624 A | 2/1989 | Yao et al. | |
| 4,813,424 A | 3/1989 | Wilkins | |
| 4,815,469 A | 3/1989 | Cohen et al. | |
| 4,820,399 A | 4/1989 | Senda et al. | |
| 4,822,337 A | 4/1989 | Newhouse et al. | |
| 4,830,959 A | 5/1989 | McNeil et al. | |
| 4,832,797 A | 5/1989 | Vadgama et al. | |
| 4,840,893 A | 6/1989 | Hill et al. | |
| 4,848,351 A | 7/1989 | Finch | |
| 4,871,351 A | 10/1989 | Feingold | |
| 4,871,440 A | 10/1989 | Nagata et al. | |
| 4,890,620 A * | 1/1990 | Gough | 600/348 |
| 4,894,137 A | 1/1990 | Takizawa et al. | |
| 4,894,253 A * | 1/1990 | Heineman et al. | 427/498 |
| 4,897,162 A | 1/1990 | Lewandowski et al. | |
| 4,897,173 A | 1/1990 | Nankai et al. | |
| 4,909,908 A | 3/1990 | Ross et al. | |
| 4,911,794 A | 3/1990 | Parce et al. | |
| 4,919,141 A | 4/1990 | Zier et al. | |
| 4,919,767 A | 4/1990 | Vadgama et al. | |
| 4,923,586 A | 5/1990 | Katayama et al. | |
| 4,927,516 A | 5/1990 | Yamaguchi et al. | |
| 4,935,105 A | 6/1990 | Churchouse | |
| 4,935,345 A | 6/1990 | Guilbeau et al. | |
| 4,936,956 A | 6/1990 | Wrighton | |
| 4,938,860 A | 7/1990 | Wogoman | |
| 4,942,127 A | 7/1990 | Wada et al. | |
| 4,945,045 A | 7/1990 | Forrest et al. | |
| 4,950,378 A | 8/1990 | Nagata | |
| 4,953,552 A | 9/1990 | DeMarzo | |
| 4,968,400 A | 11/1990 | Shimomura et al. | |
| 4,970,145 A | 11/1990 | Bennetto et al. | |
| 4,974,929 A | 12/1990 | Curry | |
| 4,986,271 A | 1/1991 | Wilkins | |
| 4,994,167 A | 2/1991 | Shults et al. | |
| 5,034,192 A | 7/1991 | Wrighton et al. | |
| 5,037,527 A | 8/1991 | Hayashi et al. | |
| 5,070,535 A | 12/1991 | Hochmair et al. | |
| 5,078,854 A | 1/1992 | Burgess et al. | |
| 5,082,550 A | 1/1992 | Rishpon et al. | |
| 5,082,786 A | 1/1992 | Nakamoto | |
| 5,089,112 A | 2/1992 | Skotheim et al. | |
| 5,094,951 A | 3/1992 | Rosenberg | |
| 5,096,560 A | 3/1992 | Takai et al. | |
| 5,096,836 A | 3/1992 | Macho et al. | |
| 5,101,814 A | 4/1992 | Palti | |
| 5,108,564 A | 4/1992 | Szuminsky et al. | |
| 5,109,850 A | 5/1992 | Blanco et al. | |
| 5,120,420 A | 6/1992 | Nankai et al. | |
| 5,120,421 A | 6/1992 | Glass et al. | |
| 5,126,034 A | 6/1992 | Carter et al. | |
| 5,126,247 A | 6/1992 | Palmer et al. | |
| 5,130,009 A | 7/1992 | Marsoner et al. | |
| 5,133,856 A | 7/1992 | Yamaguchi et al. | |
| 5,140,393 A | 8/1992 | Hijikihigawa et al. | |
| 5,141,868 A | 8/1992 | Shanks et al. | |
| 5,161,532 A | 11/1992 | Joseph | |
| 5,165,407 A | 11/1992 | Wilson et al. | |
| 5,168,046 A | 12/1992 | Hamamoto et al. | |
| 5,174,291 A | 12/1992 | Schoonen et al. | |
| 5,185,256 A | 2/1993 | Nankai et al. | |
| 5,192,415 A | 3/1993 | Yoshioka et al. | |

| Patent Number | Date | Inventor |
|---|---|---|
| 5,192,416 A | 3/1993 | Wang et al. |
| 5,198,367 A | 3/1993 | Aizawa et al. |
| 5,200,051 A | 4/1993 | Cozzette et al. |
| 5,202,261 A | 4/1993 | Musho et al. |
| 5,205,920 A | 4/1993 | Oyama et al. |
| 5,206,145 A | 4/1993 | Cattell |
| 5,208,154 A | 5/1993 | Weaver et al. |
| 5,217,595 A | 6/1993 | Smith et al. |
| 5,227,042 A | 7/1993 | Zawodzinski et al. |
| 5,229,282 A | 7/1993 | Yoshioka et al. |
| 5,250,439 A | 10/1993 | Musho et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,105 A * | 11/1993 | Gregg et al. .......... 204/403.09 |
| 5,264,106 A | 11/1993 | McAleer et al. |
| 5,271,815 A | 12/1993 | Wong |
| 5,272,060 A | 12/1993 | Hamamoto et al. |
| 5,278,079 A | 1/1994 | Gubinski et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,293,546 A | 3/1994 | Tadros et al. |
| 5,310,885 A | 5/1994 | Maier et al. |
| 5,320,725 A | 6/1994 | Gregg et al. |
| 5,326,449 A | 7/1994 | Cunningham |
| 5,337,747 A | 8/1994 | Neftel |
| 5,352,348 A | 10/1994 | Young et al. |
| 5,356,786 A | 10/1994 | Heller et al. |
| 5,364,797 A | 11/1994 | Olson et al. |
| 5,368,028 A | 11/1994 | Palti |
| 5,372,133 A | 12/1994 | Hogen Esch |
| 5,378,628 A | 1/1995 | Gratzel et al. |
| 5,380,422 A | 1/1995 | Negishi et al. |
| 5,382,346 A | 1/1995 | Uenoyama et al. |
| 5,387,327 A | 2/1995 | Khan |
| 5,390,671 A | 2/1995 | Lord et al. |
| 5,391,250 A | 2/1995 | Cheney, II et al. |
| 5,393,903 A | 2/1995 | Gratzel et al. |
| 5,395,504 A | 3/1995 | Saurer et al. |
| 5,411,647 A | 5/1995 | Johnson et al. |
| 5,413,690 A | 5/1995 | Kost et al. |
| 5,422,246 A | 6/1995 | Koopal et al. |
| 5,437,973 A | 8/1995 | Vadgama et al. |
| 5,437,999 A | 8/1995 | Diebold et al. |
| 5,478,751 A | 12/1995 | Oosta et al. |
| 5,494,562 A | 2/1996 | Maley et al. |
| 5,496,453 A | 3/1996 | Uenoyama et al. |
| 5,497,772 A | 3/1996 | Schulman et al. |
| 5,501,956 A | 3/1996 | Wada et al. |
| 5,507,288 A | 4/1996 | Bocker et al. |
| 5,508,171 A | 4/1996 | Walling et al. |
| 5,514,253 A | 5/1996 | Davis et al. |
| 5,520,787 A | 5/1996 | Hanagan et al. |
| 5,525,511 A | 6/1996 | D'Costa |
| 5,526,120 A | 6/1996 | Jina et al. |
| 5,531,878 A | 7/1996 | Vadgama et al. |
| 5,552,027 A | 9/1996 | Birkle et al. |
| 5,556,524 A | 9/1996 | Albers |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,575,895 A | 11/1996 | Ikeda et al. |
| 5,580,527 A | 12/1996 | Bell et al. |
| 5,582,184 A | 12/1996 | Erickson et al. |
| 5,582,697 A | 12/1996 | Ikeda et al. |
| 5,582,698 A | 12/1996 | Flaherty et al. |
| 5,586,553 A | 12/1996 | Halili et al. |
| 5,589,326 A | 12/1996 | Deng et al. |
| 5,593,852 A * | 1/1997 | Heller et al. .......... 435/14 |
| 5,596,150 A | 1/1997 | Arndt et al. |
| 5,617,851 A | 4/1997 | Lipkovker |
| 5,628,890 A | 5/1997 | Carter et al. |
| 5,650,062 A | 7/1997 | Ikeda et al. |
| 5,651,869 A | 7/1997 | Yoshioka et al. |
| 5,660,163 A | 8/1997 | Schulman et al. |
| 5,670,031 A | 9/1997 | Hintsche et al. |
| 5,680,858 A | 10/1997 | Hansen et al. |
| 5,682,233 A | 10/1997 | Brinda |
| 5,695,623 A | 12/1997 | Michel et al. |
| 5,695,947 A | 12/1997 | Guo et al. |
| 5,708,247 A | 1/1998 | McAleer et al. |
| 5,711,861 A * | 1/1998 | Ward et al. .......... 600/347 |
| 5,711,862 A | 1/1998 | Sakoda et al. |
| 5,720,862 A | 2/1998 | Hamamoto et al. |
| 5,727,548 A | 3/1998 | Hill et al. |
| 5,741,211 A | 4/1998 | Renirie et al. |
| 5,741,688 A | 4/1998 | Oxenboll et al. |
| 5,746,217 A | 5/1998 | Erickson et al. |
| 5,770,028 A | 6/1998 | Maley et al. |
| 5,791,344 A * | 8/1998 | Schulman et al. .......... 600/347 |
| 5,804,048 A * | 9/1998 | Wong et al. .......... 204/403.09 |
| 5,820,570 A | 10/1998 | Erickson et al. |
| 5,830,341 A | 11/1998 | Gilmartin |
| 5,834,224 A | 11/1998 | Ruger et al. |
| 5,837,454 A | 11/1998 | Cozzette et al. |
| 5,842,983 A | 12/1998 | Abel et al. |
| 5,846,702 A | 12/1998 | Deng et al. |
| 5,846,744 A | 12/1998 | Athey et al. |
| 5,857,983 A | 1/1999 | Douglas et al. |
| 5,879,311 A | 3/1999 | Duchon et al. |
| 5,951,492 A | 9/1999 | Douglas et al. |
| 5,951,493 A | 9/1999 | Douglas et al. |
| 6,004,441 A | 12/1999 | Fujiwara et al. |
| 6,033,866 A | 3/2000 | Guo et al. |
| 6,063,039 A | 5/2000 | Cunningham et al. |
| 6,071,391 A | 6/2000 | Gotoh et al. |
| 6,103,033 A | 8/2000 | Say et al. |
| 6,119,028 A * | 9/2000 | Schulman et al. .......... 600/345 |
| 6,120,676 A | 9/2000 | Heller et al. |
| 6,134,461 A | 10/2000 | Say et al. |
| 6,143,164 A | 11/2000 | Heller et al. |
| 6,175,752 B1 | 1/2001 | Say et al. |
| 6,284,125 B1 * | 9/2001 | Hodges et al. .......... 205/775 |

FOREIGN PATENT DOCUMENTS

| | | |
|---|---|---|
| EP | 0 078 636 A1 | 5/1983 |
| EP | 0 096 288 A1 | 12/1983 |
| EP | 0 125 139 A2 | 11/1984 |
| EP | 0 136 362 A1 | 4/1985 |
| EP | 0 170 375 A2 | 2/1986 |
| EP | 0 080 304 B1 | 5/1986 |
| EP | 0 184 909 A2 | 6/1986 |
| EP | 0 206 218 A2 | 12/1986 |
| EP | 0 230 472 A1 | 8/1987 |
| EP | 0 241 309 A3 | 10/1987 |
| EP | 0 245 073 A2 | 11/1987 |
| EP | 0 278 647 A2 | 8/1988 |
| EP | 0 286 084 A2 | 10/1988 |
| EP | 0 359 831 A1 | 3/1990 |
| EP | 0 368 209 A1 | 5/1990 |
| EP | 0 390 390 A1 | 10/1990 |
| EP | 0 400 918 A1 | 12/1990 |
| EP | 0 453 283 A1 | 10/1991 |
| EP | 0 470 290 A1 | 2/1992 |
| EP | 0 255 291 B1 | 6/1992 |
| EP | 0 127 958 B2 | 4/1996 |
| EP | 0 781 406 B1 | 5/1998 |
| GB | 1394 171 | 5/1975 |
| GB | 2 073 891 A | 10/1981 |
| GB | 2 154 003 B | 8/1985 |

| | | |
|---|---|---|
| GB | 2 204 408 A | 11/1988 |
| JP | 54-41191 | 4/1979 |
| JP | 55-10581 | 1/1980 |
| JP | 55-10583 | 1/1980 |
| JP | 55-10584 | 1/1980 |
| JP | 55-12406 | 1/1980 |
| JP | 56-163447 | 12/1981 |
| JP | 57-70448 | 4/1982 |
| JP | 60-173457 | 9/1985 |
| JP | 60-173458 | 9/1985 |
| JP | 60-173459 | 9/1985 |
| JP | 61-90050 | 5/1986 |
| JP | 62-85855 | 4/1987 |
| JP | 62 114747 | 5/1987 |
| JP | 63-58149 | 3/1988 |
| JP | 63-128252 | 5/1988 |
| JP | 63-139246 | 6/1988 |
| JP | 63-294799 | 12/1988 |
| JP | 63-317758 | 12/1988 |
| JP | 1-114746 | 5/1989 |
| JP | 1-114747 | 5/1989 |
| JP | 1-134244 | 5/1989 |
| JP | 1-156658 | 6/1989 |
| JP | 2-62958 | 3/1990 |
| JP | 2-120655 | 5/1990 |
| JP | 2-287145 | 11/1990 |
| JP | 2-310457 | 12/1990 |
| JP | 3-26956 | 2/1991 |
| JP | 3-28752 | 2/1991 |
| JP | 3-202764 | 9/1991 |
| JP | 5-72171 | 3/1993 |
| JP | 5-196595 | 8/1993 |
| SU | 1281988 A1 | 1/1987 |
| WO | WO 85/05119 | 11/1985 |
| WO | WO 89/08713 | 9/1989 |
| WO | WO 90/05300 | 5/1990 |
| WO | WO 91/04704 | 4/1991 |
| WO | WO 91/09139 | 6/1991 |
| WO | WO 92/13271 | 8/1992 |
| WO | WO 94/20602 | 9/1994 |
| WO | WO 94/27140 | 11/1994 |
| WO | WO 95/02817 | 1/1995 |
| WO | WO 97/00441 | 1/1997 |
| WO | WO 97/18464 | 5/1997 |
| WO | WO 97/19344 | 5/1997 |
| WO | WO 97/42882 | 11/1997 |
| WO | WO 97/42883 | 11/1997 |
| WO | WO 97/42886 | 11/1997 |
| WO | WO 97/42888 | 11/1997 |
| WO | WO 97/43962 | 11/1997 |
| WO | WO 98/35225 | 8/1998 |
| WO | WO 99/08106 | 2/1999 |
| WO | WO 99/30152 | 6/1999 |
| WO | WO 99/38003 | 7/1999 |
| WO | WO 99/45375 | 9/1999 |
| WO | WO 99/45387 | 9/1999 |
| WO | WO 99/56613 | 11/1999 |

OTHER PUBLICATIONS

Albery, W. J. et al., "Amperometric Enzyme Electrodes," *Phil. Trans. R. Soc. Lond.* B316:107–119 (1987).

Alcock, S. J. et al., "Continuous Analyte Monitoring to Aid Clinical Practice," *IEEE Engineering in Medicine and Biology*, 319–325 (1994).

Anderson, L. B. et al., "Thin–Layer Electrochemistry: Steady–State Methods of Studying Rate Processes," *J. Electroanal. Chem.*, 10:295–305 (1965).

Bartlett, P. N. et al., "Covalent Binding of Electron Relays to Glucose Oxidation," *J. Chem. Soc. Chem. Commun.*, 1603–1604 (1987).

Bartlett, P. N. et al., "Modification of glucose oxidase by tetrathiafulvalene," *J. Chem. Soc., Chem. Commun.*, 16 (1 page—Abstract only) (1990).

Bartlett, P. N. et al., "Strategis for the Development of Amperometric Enzyme Electrodes," *Biosensors*, 3:359–379 (1987/88).

Bobbioni–Harsch, E. et al., "Lifespan of subcutaneous glucose sensors and their performances during dynamic glycaemia changes in rats," *J. Biomed. Eng.* 15:457–463 (1993).

Brandt, J. et al., "Covalent attachment of proteins to polysaccharide carriers by means of benzoquinone," *Biochim. Biophys. Acta*, 386(1) (1 page Abstract only) (1975).

Brownlee, M. et al., "A Glucose–Controlled Insulin–Delivery System: Semisynthetic Insulin Bound to Lectin", *Science*, 206(4423):1190–1191 (Dec. 7, 1979).

Cass, A.E.G. et al., "Ferricinum Ion As An Electron Acceptor for Oxido–Reductases," *J. Electroanal. Chem.*, 190:117–127 (1985).

Cass, A.E.G. et al., "Ferrocene–Mediated Enzyme Electrode for Amperometric Determination of Glucose", *Anal. Chem.*, 56(4):667–671 (Apr. 1984).

Castner, J. F. et al., "Mass Transport and Reaction Kinetic Parameters Determined Electrochemically for Immobilized Glucose Oxidase," *Biochemistry*, 23(10):2203–2210 (1984).

Claremont, D.J. et al., "Biosensors for Continuous In Vivo Glucose Monitoring", *IEEE Engineering in Medicine and Biology Society 10th Annual International Conference*, New Orleans, Louisiana, 3 pgs. (Nov. 4–7, 1988).

Chen, C.Y. et al., "A Biocompatible Needle–Type Glucose Sensor Based on Platinum–Electroplated Carbon Electrode", *Applied Biochemistry and Biotechnology*, 36:211–226 (1992).

Chen, C.Y. et al., "Amperometric Needle–Type Glucose Sensor based on a Modified Platinum Electrode with Diminished Response to Interfering Materials", *Analytica Chimica Acta*, 265:5–14 (1992).

Clark, L.C. et al., "Differential Anodic Enzyme Polarography for the Measurement of Glucose", *Oxygen Transport to Tissue: Instrumentation, Methods, and Physiology*, 127:133 (1973).

Clark, L.C., Jr. et al., "Electrode Systems for Continuous Monitoring in Cardiovascular Surgery," *Annals New York Academy of Sciences*, pp. 29–45 (1962).

Clarke, W.L., et al., "Evaluating Clinical Accuracy of Systems for Self–Monitoring of Blood Glucose," *Diabetes Care*, 10(5):622–628 (Sep.–Oct. 1987).

Csöregi, E. et al., "Design, Characterization, and One–Point in Vivo Calibration of a Subcutaneously Implanted Glucose Electrode," *Anal. Chem.* 66(19):3131–3138 (Oct. 1, 1994).

Csöregi, E. et al., "On–Line Glucose Monitoring by Using Microdialysis Sampling and Amperometric Detection Based on "Wired" Glucose Oxidase in Carbon Paste," *Mikrochim. Acta*. 121:31–40 (1995).

Davis, G., "Electrochemical Techniques for the Development of Amperometric Biosensors", *Biosensors*, 1:161–178 (1985).

Degani, Y. et al., "Direct Electrical Communication between Chemically Modified Enzymes and Metal Electrodes. 1. Electron Transfer from Glucose Oxidase to Metal Electrodes via Electron Relays, Bound Covalently to the Enzyme,"*J. Phys. Chem.*, 91(6):1285–1289 (1987).

Degani, Y. et al., "Direct Electrical Communication between Chemically Modified Enzymes and Metal Electrodes. 2. Methods for Bonding Electron–Transfer Relays to Glucose Oxidase and D–Amino–Acid Oxidase," *J. Am. Chem. Soc.*, 110(8):2615–2620 (1988).

Degani, Y. et al., "Electrical Communication between Redox Centers of Glucose Oxidase and Electrodes via Electrostatically and Covalently Bound Redox Polymers," *J. Am. Chem. Soc.*, 111:2357–2358 (1989).

Denisevich, P. et al., "Unidirectional Current Flow and Charge State Trapping at Redox Polymer Interfaces on Bilayer Electrodes: Principles, Experimental Demonstration, and Theory," *J. Am. Chem. Soc.*, 103(16):4727–4737 (1981).

Dicks, J. M., "Ferrocene modified polypyrrole with immobilised glucose oxidase and its application in amperometric glucose microbiosensors," *Ann. Biol. clin.*, 47:607–619 (1989).

Engstrom, R.C., "Electrochemical Pretreatment of Glassy Carbon Electrodes", *Anal. Chem.*, 54(13):2310–2314 (Nov. 1982).

Engstrom, R.C. et al., "Characterization of Electrochemically Pretreated Glassy Carbon Electrodes", *Anal. Chem.*, 56(2):136–141 (Feb. 1984).

Ellis, C. D., "Selectivity and Directed Charge Transfer through an Electroactive Metallopolymer Film," *J. Am. Chem. Soc.*, 103(25):7480–7483 (1981).

Fischer, H. et al., "Intramolecular Electron Transfer Mediated by 4,4'–Bipyridine and Related Bridging Groups", *J. Am. Chem. Soc.*, 98(18):5512–5517 (Sep. 1, 1976).

Foulds, N.C. et al., "Enzyme Entrapment in Electrically Conducting Polymers," *J. Chem. Soc., Faraday Trans 1.*, 82:1259–1264 (1986).

Foulds, N.C. et al., "Immobilization of Glucose Oxidase in Ferrocene–Modified Pyrrole Polymers," *Anal. Chem.*, 60(22):2473–2478 (Nov. 15, 1988).

Frew, J.E. et al., "Electron–Transfer Biosensors", *Phil. Trans. R. Soc. Lond.*, B316:95–106 (1987).

Gernet, S. et al., "Fabrication and Characterization of a Planar Electrochemical Cell and Its Application as a Glucose Sensor", *Biosensors & Actuators*, 18:59–70 (1989).

Gorton, L. et al., "Selective detection in flow analysis based on the combination of immobilized enzymes and chemically modified electrodes," *Analytica Chimica Acta.*, 250:203–248 (1991).

Gregg, B. A. et al., "Cross–Linked Redox Gels Containing Glucose Oxidase for Amperometric Biosensor Applications," *Analytical Chemistry*, 62(3):258–263 (Feb. 1, 1990).

Gregg, B. A. et al., "Redox Polymer Films Containing Enzymes. 1. A Redox–Conducting Epoxy Cement: Synthesis, Characterization, and Electrocatalytic Oxidation of Hydroquinone," *J. Phys. Chem.*, 95(15):5970–5975 (1991).

Hale, P.D. et al., "A New Class of Amperometric Biosensor Incorporating a Polymeric Electron–Transfer Mediator," *J. Am. Chem. Soc.*, 111(9):3482–3484 (1989).

Harrison, D.J. et al., "Characterization of Perfluorosulfonic Acid Polymer Coated Enzyme Electrodes and a Miniaturized Integrated Potentiostat for Glucose Analysis in Whole Blood", *Anal. Chem.*, 60(19):2002–2007 (Oct. 1, 1988).

Hawkridge, F. M. et al., "Indirect Coulometric Titration of Biological Electron Transport Components," *Analytical Chemistry*, 45(7):1021–1027 (Jun. 1973).

Heineman, W.R. et al., "Measurement of Enzyme $E^{o\prime}$ Values by Optically Transparent Thin Layer Electrochemical Cells", *Analytical Chemistry*, 47(1):79, 82–84 (Jan. 1975).

Heineman, W.R. "Spectro–electro–chemistry", *Analytical Chemistry*, 50(3):390–392, 394, 396, 398, 400, 402 (Mar. 1978).

Heller, A., "Amperometric biosensors based on three–dimensional hydrogel–forming epoxy networks," *Sensors and Actuators B*, 13–14:180–183 (1993).

Heller, A., "Electrical Connection of Enzyme Redox Centers to Electrodes," *J. Phys. Chem,*, 96(9):3579–3587 (1992).

Heller, A., "Electrical Wiring of Redox Enzymes," *Acc. Chem. Res.*, 23(5):129–134 (1990).

Ianniello, R.M. et al. "Immobilized Enzyme Chemically Modified Electrode as an Amperometric Sensor", *Anal. Chem.*, 53(13):2090–2095 (Nov. 1981).

Ianniello, R.M. et al., "Differential Pulse Voltammetric Study of Direct Electron Transfer in Glucose Oxidase Chemically Modified Graphite Electrodes", *Anal. Chem.*, 54:(7):1098–1101 (Jun. 1981).

Ikeda, T. et al., "Glucose oxidase–immobilized benzoquinone–carbon paste electrode as a glucose sensor," *Agric. Biol. Chem.*, 49(2) (1 page—Abstract only) (1985).

Johnson, J. M. et al., "Potential–Dependent Enzymatic Activity in an Enzyme Thin–Layer Cell," *Anal. Chem.* 54:1377–1383 (1982).

Johnson K. W. et al., "In Vivo Evaluation of an Electroenzymatic Glucose Sensor Implanted in Subcutaneous Tissue", *Biosensors & bioelectronics* 7:709–714 (1992).

Johnson, K. W., "Reproducible Electrodeposition of Biomolecules for the Fabrication of Miniature Electroenzymatic Biosensors", *Sensors and Actuators B Chemical*, B5:85–89 (1991).

Jönsson, G. et al., "An Amperometric Glucose Sensor Made by Modification of a Graphite Electrode Surface With Immobilized Glucose Oxidase and Adsorbed Mediator", *Biosensors*, 1:355–368 (1985).

Josowicz, M. et al., "Electrochemical Pretreatment of Thin Film Platinum Electrodes", *J. Elecrochem. Soc.*, 135(1):112–115 (Jan. 1988).

Katakis, I. et al., "Electrostatic Control of the Electron Transfer Enabling Binding of Recombinant Glucose Oxidase and Redox Polyelectrolytes," *J. Am. Chem. Soc.*, 116(8):3617–3618 (1994).

Katakis, I. et al., "L–α–Glycerophosphate and L–Lactate Electrodes Based on the Electrochemical "Wiring" of Oxidases," *Analytical Chemistry*, 64(9):1008–1013 (May 1, 1992).

Kenausis, G. et al., "Wiring' of glucose oxidase and lactate oxidase within a hydrogel made with poly(vinyl pyridine) complexed with $[Os(4,4'-dimethoxy-2,2'-bipyridine)_2Cl]^{+/2+}$," *J. Chem. Soc., Faraday Trans.*, 92(20):4131–4136 (1996).

Kondo, T. et al., "A Miniature Glucose Sensor, Implantable in the Blood Stream", *Diabetes Care*, 5(3):218–221 (May–Jun. 1982).

Kulys, J. et al., "Mediatorless peroxidase electrode and preparation of bienzyme sensors," *Bioelectrochemistry and Bioenergetics*, 24:305–311 (1990).

Lager, W. et al., "Implantable Electrocatalytic Glucose Sensor," *Horm. Metab. Res.*, 26:526–530 (Nov. 1994).

Lee, J. et al., "A New Glucose Sensor using Microporous Enzyme Membrane", *Sensors and Actuators*, B3:215–219 (1991).

Lewandowski, J.J. et al., "Evaluation of a Miniature Blood Glucose Sensor", *Trans Am Soc Artif Intern Organs*, XXXIV:255–258 (1988).

Lindner, E. et al., "Flexible (Kapton–Based) Microsensor Arrays of High Stability for Cardiovascular Applications", *J. Chem. Soc.Faraday Trans.*, 89(2):361–367 (Jan. 21, 1993).

Maidan, R. et al., "Elimination of Electrooxidizable Interferant–Produced Currents in Amperometric Biosensors," *Analytical Chemistry*, 64(23):2889–2896 (Dec. 1, 1992).

Mann–Buxbaum, E. et al, "New Microminiaturized Glucose Sensors Using Covalent Immobilization Techniques", *Sensors and Actuators*, B1:518–522 (1990).

Mastrototaro, J.J. et al., "An Electroenzymatic Glucose Sensor Fabricated on a Flexible Substrate", *Sensors and Biosensors B Chemical*, B5:139–144 (1991).

Matthews, D.R., et al., "An Amperometric Needle–Type Glucose Sensor Tested in Rats and Man", *Original Articles*, pp. 248–252 (1988).

McKean et al., "A telemetry–Instrumentation System for Chronically Implanted Glucose and Oxygen Sensors", *IEEE Transactions of Biomedical Engineering*, 35(7):526–532 (Jul. 1988).

McNeil, C. J. et al., "Thermostable Reduced Nicotinamide Adenine Dinucleotide Oxidase: Application to Amperometric Enzyme Assay," *Anal. Chem.*, 61(1):25–29 (Jan. 1, 1989).

Miyawaki, O. et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, 838:60–68 (1985).

Moatti–Sirat, D. et al., "Evaluating in vitro and in vivo the inteference of ascorbate and acetaminophen on glucose detection by a needle–type glucose sensors," *Biosensors & Bioelectronics*, 7(5):345–352 (1992).

Moatti–Sirat, D. et al., "Reduction of acetaminophen interference in glucose sensors by a composite Nafion membrane: demonstration in rats and man," *Diabetologia*, 37(6) (1 page—Abstract only) (Jun. 1994).

Moatti–Sirat, D. et al., "Towards continous glucose monitoring: in vivo evaluation of a miniaturized glucose sensor implanted for several days in rat subcutaneous tissue," *Diabetologia*, 35(3) (1 page—Abstract only) (Mar. 1992).

Moser, I. et al., "Advanced Immobilization and Protein Techniques on thin Film Biosensors", *Sensors and Actuators*, B7:356–362 (1992).

Moussy, F. et al., "Performance of Subcutaneously Implanted Needle–Type Glucose Sensors Employing a Novel Trilayer Coating", *Anal. Chem.*, 65:2072–2077 (1993).

Nagy, G. et al., "A New Type of Enzyme Electrode: The Ascorbic Acid Eliminator Electrode," *Life Sciences*, 31(23):2611–2616 (1982).

Nakamura, S. et al., "Effects of Periodate Oxidation on the Structure and Properties of Glucose Oxidase," *Biochimica et Biophysica Acta.*, 445:294–308 (1976).

Narasimhan, K. et al., "p–Benzoquinone activation of metal oxide electrodes for attachement of enzymes," *Enzyme Microb. Technol.*, 7(6) (1 page—Abstract only) (1985).

Ohara, T.J. et al., "Glucose Electrodes Based on Cross–Linked [Os(bpy)$_2$Cl]$^{+/2+}$ Complexed Poly(1–vinylimadazole) Films," *Analytical Chemistry*, 65(23):3512–3516 (Dec. 1, 1993).

Ohara, T.J., "Osmium Bipyridyl Redox Polymers Used in Enzyme Electrodes," *Platinum Metals Rev.*, 39(2):54–62 (Apr. 1995).

Ohara, T. J. et al., ""Wired" Enzyme Electrodes for Amperometric Determination of Glucose or Lactate in the Presence of Interfering Substances," *Analytical Chemistry*, 66(15):2451–2457 (Aug. 1, 1994).

Olievier, C. N. et al., "In vivo Measurement of Carbon Dioxide Tension with a Miniature Electrode," *Pflugers Arch.* 373:269–272 (1978).

Paddock, R. et al., "Electrocatalytic reduction of hydrogen peroxide via direct electron transfer from pyrolytic graphite electrodes to irreversibly adsorbed cytochrome c peroxidase," *J. Electroanal. Chem.*, 260:487–494 (1989).

Palleschi, G. et al., "A Study of Interferences in Glucose Measurements in Blood by Hydrogen Peroxide Based Glucose Probes", *Anal. Biochem.*, 159:114–121 (1986).

Palleschi, G. et al., "Ideal Hydrogen Peroxide–Based Glucose Sensor", *Applied Biochemistry and Biotechnology*, 31:21–35 (1991).

Pankratov, I. et al., "Sol–gel derived renewable–surface biosensors," *Journal of Electroanalytical Chemistry*, 393:35–41 (1995).

Pathak, C. P. et al., "Rapid Photopolymerization of Immunoprotective Gels in Contact with Cells and Tissue," *J. Am. Chem. Soc.*, 114(21):8311–8312 (1992).

Pickup, J. et al., "Potentially–implantable, amperometric glucose sensors with mediated electron transfer: improving the operating stability," *Biosensors*, 4(2) (1 page—Abstract only) (1989).

Pishko, M.V. et al., "Amperometric Glucose Microelectrodes Prepared Through Immobilization of Glucose Oxidase in Redox Hydrogels", *Anal. Chem.*, 63(20):2268–2272 (Oct. 15, 1991).

Poitout, V. et al., "A glucose monitoring system for on line estimation in man of blood glucose concentration using a miniaturized glucose sensor implanted in the subcutaneous tissue and a wearable control unit," *Diabetolgia*, 36(7) (1 page—Abstract only) (Jul. 1993).

Poitout, V. et al., "Calibration in dogs of a subcutaneous miniaturized glucose sensor using a glucose meter for blood glucose determination," *Biosensors & Bioelectronics*, 7:587–592 (1992).

Poitout, V. et al., "In vitro and in vivo evaluation in dogs of a miniaturized glucose sensor," *ASAIO Transactions*,37(3) (1 page—Abstract only) (Jul.–Sep. 1991).

Pollak, A. et al., "Enzyme Immobilization by Condensation Copolymerization into Cross–Linked Polyacrylamide Gels," *J. Am. Chem. Soc.*,102(20):6324–6336 (1980).

Pons, B. S. et al., "Application of Deposited Thin Metal Films as Optically Transparent Electrodes for Internal Reflection Spectrometric Observation of Electrodes Solution Interfaces", *Analytical Chemistry*, 39(6):685–688, (May 1967).

Reach, G. et al., "A Method for Evaluating in vivo the Functional Characteristics of Glucose Sensors", *Biosensors* 2:211–220 (1986).

Reach, G. et al., "Can Continuous Glucose Monitoring Be Used for the Treatment of Diabetes?" *Analytical Chemistry*, 64(6):381–386 (Mar. 15, 1992).

Rebrin, K. et al., "Automated Feedback Control of Subcutaneous Glucose Concentration in Diabetic Dogs", *Diabetologia*, 32(8):573–576 (Aug. 1989).

Sasso, S.V. et al., "Electropolymerized 1,2–Diaminobenzene as a Means to Prevent Interferences and Fouling and to Stabilize Immobilized Enzyme in Electrochemical Biosensors", *Anal. Chem.*, 62(11):1111–1117 (Jun. 1, 1990).

Schalkhammer, T. et al, "Electrochemical Glucose Sensors on Permselective Non–conducting Substitute Pyrrole Polymers", *Sensors and Actuators*, B4:273–281 (1991).

Scheller, F. et al., "Enzyme electrodes and their application," *Phil. Trans. R. Soc. Lond.*, B 316:85–94 (1987).

Shichiri, M. et al., "Glycaemic Control in Pancreatetomized Dogs with a Wearable Artificial Endocrine Pancreas", *Diabetologia*, 24(3):179–184 (Mar. 1983).

Shigeru, T. et al, "Simultaneous Determination of Glucse and 1,5–= Anydroglucitol", *Chemicl Abstracts*, 111:394 (1989).

Sittampalam, G. et al., "Surface–Modified Electrochemical Detector of Liquid Chromatography", *Anal. Chem.*, 55(9):1608–1610 (Aug. 1983).

Soegijoko, S. et al., *Horm. Metabl. Res., Suppl. Ser*, 12 (1 page—Abstract only) (1982).

Sprules, S. D. et al., "Evaluation of a New Disposable Screen–Printed Sensor Strip for the Measurement of NADH and Its Modification to Produce a Lactate Biosensor Employing Microliter Volumes," *Electroanalysis*, 8(6):539–543 (1996).

Sternberg, F. et al., "Calibration Problems of Subcutaneous Glucosensors when Applied "In–Situ" in Man," *Horm. metabl. Res*, 26:523–525 (1994).

Sternberg, R. et al., "Covalent Enzyme Coupling on Cellulose Acetate Membranes for Glucose Sensor Development," *Analytical Chemistry*, 60(24):2781–2786 (Dec. 15, 1988).

Suekane, M., "Immobilization of glucose isomerase," *Zeitschrift für Allgemeine Mikrobiologie*, 22(8):565–576 (1982).

Tarasevich, M.R. "Bioelectrocatalysis", *Comprehensive Treatise of Electrochemistry*, 10 (Ch. 4):231–295 (1985).

Taylor, C. et al., "Wiring' of glucose oxidase within a hydrogel made with polyvinyl imidazole complexed with [(Os–4,4'–dimethoxy–2,2'–bipyridine)Cl]$^{+/2+}$," *Journal of Electroanalytical Chemistry*, 396:511–515 (1995).

Trojanowicz, M. et al., "Enzyme Entrapped Polypyrrole Modified Electrode for Flow–Injection Determination of Glucose," *Biosensors & Bioelectronics*, 5:149–156 (1990).

Turner, A.P.F. et al., "Diabetes Mellitus: Biosensors for Research and Management", *Biosensors*, 1:85–115 (1985).

Turner, R. F. B. et al., "A Biocompatible Enzyme Electrode for Continous in vivo Glucose Monitoring in Whole Blood," *Sensors and Actuators*, B1(1–6):561–564 (Jan. 1990).

Umaha, M., "Protein–Modified Electrochemically Active Biomaterial Surface," *U.S. Army Research Office Report*, (12 pages) (Dec. 1988).

Urban, G. et al., "Miniaturized Thin–Film Biosensors Using Covalently Immobilized Glucose Oxidase", *Biosensors & Bioelectronics*, 6(7):555–562 (1991).

Velho, G. et al., "Strategies for calibrating a subcutaneous glucose sensor," *Biomed. Biochin. Acta*, 48(11/12):957–964 (1989).

Vidal, J.C. et al., "A chronoamperometric sensor for hydrogen peroxide based on electron transfer between immobilized horseradish peroxidase on a glassy carbon electrode and a diffusing ferrocene mediator", *Sensors and Actuators B 21*, pp. 135–141 (1994).

Von Woedtke, T. et al., "In Situ Calibration of Implanted Electrochemical Glucose Sensors," *Biomed. Biochim. Acta*, 48(11/12):943–952 (1989).

Vreeke, M. S. et al., "Chapter 15: Hydrogen Peroxide Electrodes Based on Electrical Connection of Redox Centers of Various Peroxidases to Electrodes through a Three–Dimensional Electron–Relaying Polymer Network," *Diagnostic Biosensor Polymers*, 7 pgs. (Jul. 26, 1993).

Vreeke, M. et al., "Hydrogen Peroxide and β–Nicotinamide Adenine Dinucleotide Sensing Amperometric Electrodes Based on Electrical Connection of Horseradish Peroxidase Redox Centers to Electrodes through a Three–Dimensional Electron Relaying Polymer Network," *Analytical Chemistry*, 64(24):3084–3090 (Dec. 15, 1992).

Wang, J. et al., "Activation of Glassy Carbon Electrodes by Alternating Current Electrochemical Treatment", *Analytica Chimica Acta*, 167:325–334 (Jan. 1985).

Wang, J. et al., "Amperometric biosensing of organic peroxides with peroxidase–modified electrodes," *Analytica Chimica Acta*. 254:81–88 (1991).

Wang, J. et al., "Screen–Printable Sol–Gel Enzyme–Containing Carbon Inks," *Analytical Chemistry*, 68(15):2705–2708 (Aug. 1, 1996).

Wang, J. et al., "Sol–Gel–Derived Metal–Dispersed Carbon Composite Amperometric Biosensors," *Electroanalysis*, 9(1):52–55 (1997).

Williams, D.L. et al., "Electrochemical–Enzymatic Analysis of Blood Glucose and Lactate", *Anal. Chem.*, 42(1):118–121 (Jan. 1970).

Yabuki, S. et al., "Electro–conductive Enzyme Membrane," *J. Chem. Soc. Chem. Commun*, 945–946 (1989).

Yamasaki, Y., "The Development of a Needle–Type Glucose Sensor for Wearable Artificial Endocrine Pancreas", *Medical Journal of Osaka University*, vol. 35, No. 1–2, pp. 24–34 (Sep. 1994).

Yang, L. et al., "Determination of Oxidase Enzyme Substrates Using Cross–Flow Thin–Layer Amperometry," *Electroanalysis*, 8(8–9):716–721 (1996).

Yao, S.J. et al., "The Interference of Ascorbate and Urea in Low–Potential Electrochemical Glucose Sensing", *Proceedings of the Twelfth Annual International Conference of the IEEE Engineering in Medicine and Biology Society*, 12(2):487–489 (Nov. 1–4, 1990).

Yao, T. et al., "A Chemically–Modified Enzyme Membrane Electrode As An Amperometric Glucose Sensor," *Analytica Chimica Acta*, 148:27–33 (1983).

Ye, L. et al., "High Current Density "Wired" Quinoprotein Glucose Dehydrogenase Electrode," *Anal. Chem.*, 65(3):238–241 (Feb. 1, 1993).

Yildiz, A., "Evaluation of an Improved Thin–Layer Electrode", *Analytical Chemistry*, 40(7):1018–1024 (Jun. 1968).

Zamzow, K. et al., New Wearable Continuous Blood Glucose Monitor (BGM) and Artificial Pancrease (AP), *Diabetes*, 39:5A(20) (May 1990).

\* cited by examiner

US 6,654,625 B1

MASS TRANSPORT LIMITED IN VIVO ANALYTE SENSOR

RELATED APPLICATIONS

This application claims the priority of United States provisional patent application No. 60/194,618, entitled "MASS TRANSPORT LIMITED IN VIVO ANALYTE SENSOR" filed Apr. 5, 2000; and United States provisional patent application No. 60/139,936, entitled "MASS TRANSPORT LIMITED IN VIVO ANALYTE SENSOR" filed Jun. 18, 1999, both of which are incorporated herein by reference.

FIELD OF THE INVENTION

The invention relates to electrochemical analyte sensors, and more particularly to in vivo electrochemical analyte sensors.

BACKGROUND OF THE INVENTION

Subcutaneous glucose sensors based on hydrogen peroxide generation and its electrooxidation are known, for example, as described by David Gough in U.S. Pat. Nos. 4,484,987, 4,671,288, 4,890,620, 4,703,756, 4,650,547 and in Diabetes Care, vol. 5, No. 3, May–June 1982, Part 1, pp. 190–198. In these types of sensors, the production of peroxide or consumption of oxygen by enzymes (e.g., glucose oxidase) is detected on a platinum electrode. A core problem of these sensors is that the signal in such sensors is heavily dependent on a stoichiometrically adequate supply of oxygen to the sensing layer. Often, there is a relatively low concentration of oxygen in the sensing environment, as compared to glucose, which results in oxygen-dependence of the sensor.

SUMMARY OF THE INVENTION

Against this backdrop, the present invention has been developed.

In one embodiment, the invention is directed to an electrochemical sensor including a working electrode, and an analyte-responsive sensing layer proximate the working electrode. The sensing layer is exposed at or near an edge of the sensor, where the sensor signal is limited, at least in part, by mass transport of analyte to the sensing layer. The sensor is configured and arranged for implantation into the body of a mammal for contact with body fluids of the mammal.

In several embodiments of the sensor, the analyte diffuses to the sensing layer via the edge of the sensor, thereby restricting mass transport of the analyte to the sensing layer. This is because the solution-contacting surface area of the sensor edge is much smaller than an open face of the sensing layer.

In some embodiments, the edge is a peripheral edge of the sensor, for example a distal edge of the sensor. In other embodiments, the edge is a side edge of the sensor. In yet other embodiments, the sensor defines a channel having an inner peripheral surface extending into the sensor, and the edge is defined by at least a portion of the inner peripheral surface of the channel. The geometry of the sensor can be any of a broad variety of shapes, but in some embodiments the sensor is planar, and in other embodiments, the sensor is cylindrical.

In some preferred embodiments, the sensor includes a base layer and a top layer, and the sensing layer is at least partially disposed between the base layer and the top layer. Preferably, the base layer and the top layer are impervious to the analyte. In at least some embodiments, the top layer is oxygen permeable.

In another embodiment of the invention the sensor includes a sensor body having an edge, and the analyte-responsive sensing layer is disposed within the sensor body and is exposed at the edge of the sensor body. In at least some embodiments, the sensor body is impervious to analyte.

In some embodiments, sensors developed in accordance with the invention are intended for use in the subcutaneous glucose monitoring system described in U.S. Pat. No. 6,175,752, incorporated herein by reference, although they can be used with other devices and for monitoring other analytes in other parts of the body.

These and various other features as well as advantages which characterize the invention will be apparent from a reading of the following detailed description and a review of the associated drawings.

DETAILED DESCRIPTION

Sensor Structure

Figure 1:
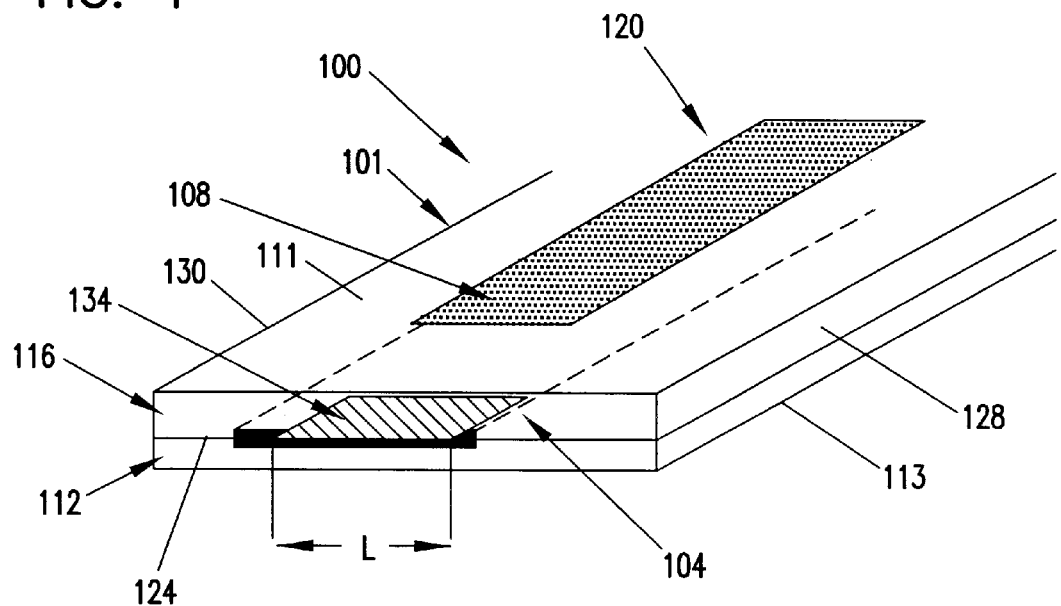
FIG. 1 is a perspective view of an analyte sensor in accordance with one embodiment of the invention.

The structure of the subcutaneously implanted portion of one embodiment of a sensor 100 is shown schematically in FIG. 1. The drawing is not to scale. The portion of the sensor 100 containing the contact pads (not shown) for the electrodes 104 and 108, which sits on the skin of a user, is not shown but can be the same as that disclosed in U.S. Pat. No. 6,175,752.

While an individual sensor 100 is shown, it will be appreciated that the sensors can be manufactured in a sheet or roll format, either in batches or in a continuous process, with many sensors on a sheet. The individual sensors are then cut from the sheet using known processes such as slitting or die cutting.

The sensor 100 includes a sensor body 101 having a top surface 111, a bottom surface 113, side edges 128 and 130, a distal edge 124, and a proximal end 120. The side edges 128 and 130 and the distaledge 124 are considered peripheral edges of the sensor body. The body also includes a working electrode 104, a reference/counter electrode 108, and a sensing layer 134. The sensor 100 includes a base layer 112 and a top layer 116. The base layer 112 is typically a thin, polymeric sheet material that is biocompatible or whose external surface has a biocompatible coating. Preferably the material is flexible. Suitable materials include, for example, polyesters and polyimides (e.g., Kapton™). Other polymers are also suitable and known to those skilled in the art. Suitable thicknesses are, for example, between 50 $\mu$m and 250 $\mu$m, although thicker or narrower materials may be used.

The working electrode 104 is formed on the base layer 112 or the top layer 116. Materials and processes for forming working electrodes 104 are known to those skilled in the art, including those materials and processes identified in U.S. Pat. No. 6,175,752 and U.S. Pat. No. 6,103,033, both of which are incorporated herein by reference. Suitable materials for working electrodes 104 include, for example, carbon, gold, platinum, palladium and other non-corroding, conductive materials. Suitable methods of depositing the conductive material, include, for example, screen printing, ink jet printing, lithographic processes, sputtering, or any other method of forming a conductive film on a surface so that its components do not leach into the body, including those described, for example, in U.S. Pat. No. 6,103,033.

At the proximal end 120 of the sensor 100 the conductive layer of the working electrode 104 terminates at a contact pad (not shown) for connection to an electronic measuring device (not shown). Near the electrochemically active portion of the sensor 100, the conductive layer of the working electrode 104 can completely cover the base layer 112 of the sensor 100, or it may only cover a portion of the base layer 112, as shown in FIG. 1. As an example, suitable widths for one embodiment of the working electrode 104 are no more than 500 $\mu$m, no more than 375 $\mu$m or no more than 250 $\mu$m, and suitable lengths between the electrochemically active portion of the sensor and the contact pad is 4 cm or less, or 2 cm or less.

It is desirable that the working electrode 104 reach at least one edge of the sensor body, preferably a peripheral edge. In the embodiment shown, the working electrode 104 reaches the distal edge 124 of the sensor body. It is also acceptable if the working electrode 104 is recessed from the edge 124, although in such a case care must be taken to ensure that the working electrode 104 is in contact with the body fluid to be analyzed either directly or through an analyte-permeable membrane. In other embodiments, it is acceptable that the working electrode 104 contact body fluids through a side edge or side edges 128 and 130 of the sensor 100 rather than through the distal tip edge 124. If all or a portion of the base layer 112 is itself conductive then the base layer 112 can serve as the working electrode.

On or near the working electrode 104 one or more sensing layers 134 are deposited, which transduce the analyte concentration into an electrical signal. A suitable sensing layer 134 includes, for example, an enzyme hydrogel, e.g., a redox polymer, an enzyme, and a cross-linker. Suitable sensing layers 134 include those described in U.S. Pat. Nos. 6,175,752, 6,143,164 (which is a continuation of abandoned application 08/795,767), and 6,338,790, and in U.S. Provisional Pat. Application No. 60/165,565, which are all incorporated herein by reference. It is preferred that the sensing chemistry be non-leachable, e.g., that no toxic, immunogenic or operationally essential materials (e.g., mediators or enzymes) leach out from the sensing layer 134 while it is implanted in the body. Such a non-leachable layer may include, for example, enzyme and/or redox mediator that is immobilized on the sensor via crosslinking, entrapment or chemical bonding. However, many other sensing chemistries are feasible, such as the peroxide sensing chemistry described below. As an example, in one embodiment, suitable sensing layer 134 thicknesses are less than 80 $\mu$m, less than 50 $\mu$m, or less than 20 $\mu$m when the sensing layer is hydrated.

As with the working electrode 104, it is preferred that the sensing layer 134 reach at least one edge of the sensor body, preferably a peripheral edge. The sensing layer 134 reaches the edge such that it is exposed to the environment external to the sensor at the edge. The sensing layer is exposed at the edge such that it can come in contact with fluid to be measured when the sensor is placed into operation. In the embodiment shown in FIG. 1, the sensing layer 134 reaches the distal edge 124 and is exposed. It is also acceptable if the sensing layer 134 is recessed from the edge, although in such a case care must be taken to ensure that the sensing layer 134 is directly or through a permeable membrane, exposed and is able to make contact with the body fluid to be analyzed.

The top layer 116 is located above the sensing layer 134. This material can be a polymeric sheet, similar to or identical to the base layer 112. Alternatively, the top layer 116 can be a polymer film formed in situ. Suitable top layers 116 that are formed in situ include UV curable polymers, elastomeric and silicone sealants, two part epoxies, pressure sensitive adhesives, polyurethanes, and water-based coatings such as polyacrylates. The top layer 116 can cover most or all of the sensor 101 (except for the contact pads) or only the portion of the sensor near the sensing layer 134. It is desirable that the top layer 116 cover as much of the implanted portion of the working electrodes 104 as possible, other than at the sensing region edge. It may be undesirable to have the working electrode 104 exposed to body fluids in the absence of the sensing layer 134, as a signal may be generated by the electrolysis of interferants such as acetaminophen, ascorbate and urate. The top layer 116 can allow passage of analyte or reactants (e.g., oxygen) through the top layer 116; more preferably, it can be impervious to the analyte. Surfaces of the top layer 116 exposed to the subcutaneous tissue should be biocompatible.

The top layer 116 can be attached to the working electrode 104 or to the base layer 112 in a variety of ways known to those skilled in the art. The most preferred method utilizes a top layer 116 that itself adheres to the working electrode 104 or base layer 112. As examples, adhesives, glues, and chemical or heat bonding can be used for top layer 116 adhesion.

The sensor 100 typically includes a counter electrode, a reference electrode, or a combined counter/reference electrode 108. One example of a suitable counter/reference electrode 108 is a silver/silver chloride electrode. Alternatively, instead of implanting the electrodes 108, the counter or counter/reference electrodes 108 can be placed on the skin using, for example, a silver/silver chloride EKG electrode. As used herein, the terms "counter electrode" and "reference electrode" include a combined counter/reference electrode. Counter or reference electrodes may be formed using a variety of materials and processes known in the art, including those in U.S. Pat. Nos. 6,175,677 and 6,103,033. These materials and processes can be the same as those used to form the working electrode described above.

The counter electrode or reference electrode 108 can be located at a variety of sites on the sensor 100, so long as it is in contact with the body fluid. In FIG. 1, a combined counter/reference electrode 108 is shown on the external surface of the top layer 116. The counter or reference electrode can be on the external surface of the base layer, or even located on an interior portion of the top or base layers, so long as it is in contact with the body fluid and it is electrically insulated from the working electrode in the absence of a sample.

In the embodiment shown in FIG. 1 the analyte diffuses to the distal or leading edge 124 of the sensor 100. It will be appreciated that the working electrode 104 and sensing layer 134 can be located at any position on the sensor 100 adjacent to an edge. This may be advantageous in order to reduce stresses and strains on the sensing edge 124 as the sensor 100 is inserted into the body or as it moves slightly in the body. For the same reason, it will be appreciated that the sensor shape need not be rectangular. Examples of suitable sensing positions include the side edges, recesses in the external perimeter of the sensor, or the edge of a hole made through the sensor that passes through the sensing layer and the working electrode.

Various methods can be employed to improve the accuracy of the sensor. For example, an interferant eliminating layer having a peroxide-generating enzyme can be deposited near the entrance of the diffusion path, with the sensing layer behind it. Examples of interferant eliminating layers are described in U.S. Pat. No. 5,262,305 and U.S. Pat. No. 5,365,786, incorporated herein by reference.

Another approach to eliminate interferants is to have a two electrode sensor. A first electrode at the diffusion path entrance is kept at a potential sufficiently high to electrolyze certain easily oxidizable interferants such as urate, ascorbate or acetaminophen. A second electrode is located behind the first electrode and serves to measure the analyte concentration. No electrical path connects these two electrodes.

One approach to minimize the contribution of interferants to current is to select a redox polymer having an oxidation potential that precludes the oxidation of interferants such as acetaminophen or urate. The selection of redox polymers that enable working electrode operation at less than +150 mV versus Ag/AgCl can reduce or prevent oxidation of acetaminophen, urate, and ascorbate. Redox polymers described in U.S. Provisional Patent Application Serial No. 60/165,565 and U.S. patent application Ser. No. 09/295,962, now issued as U.S. Pat. No. 6,338,790 both of which are incorporated herein by reference, are suitable.

The invention solves a core problem of subcutaneous glucose sensors based on hydrogen peroxide generation and its electrooxidation, such as that described by David Gough in U.S. Pat. Nos. 4,890,620, 4,703,756, 4,650,547 and in Diabetes Care, vol. 5, No. 3, May–June 1982, Part 1, pp. 190–198, all of which are hereby incorporated by reference. In this type of sensor, the production of peroxide or consumption of oxygen by enzymes (e.g., glucose oxidase) is detected on a platinum electrode using an analyte mass transport limiting structure. The problem relates to the relatively low concentration of oxygen, as compared to glucose, which results in oxygen-dependence of the sensor.

The sensors of Gough can be modified, according to the invention, to allow limited analyte flux to the sensing layer via the edge of the sensor and enhanced oxygen flux to the sensing layer via the top layer and through the sensor edge. Oxygen, smaller than glucose, will have enhanced diffusion through the sensing layer coating. Analyte flux to the sensing layer can be limited by making the sensing layer very thin and thereby reducing the area of the solution-exposed edge. Oxygen flux to the sensing layer via the top sheet material can be made high by utilizing an oxygen permeable, preferably elastomeric, top layer. Such an arrangement would address a fundamental constraint on subcutaneous glucose sensors based on peroxide detection, namely the dependence of the signal on a stoichiometrically adequate supply of oxygen to the sensing layer. Oxygen can now diffuse rapidly through the top elastomer layer. An example of a structure would include a platinum-group metal-comprising carbon film on the base layer; a thin (1–5 $\mu$m thick) layer of crosslinked enzyme (e.g. glucose oxidase) on the platinized carbon; and an oxygen-permeable polysiloxane or other elastomer coating on the enzyme layer. Such a sensor may be significantly easier to manufacture than the sensor of Gough, as well as smaller.

Figure 2:
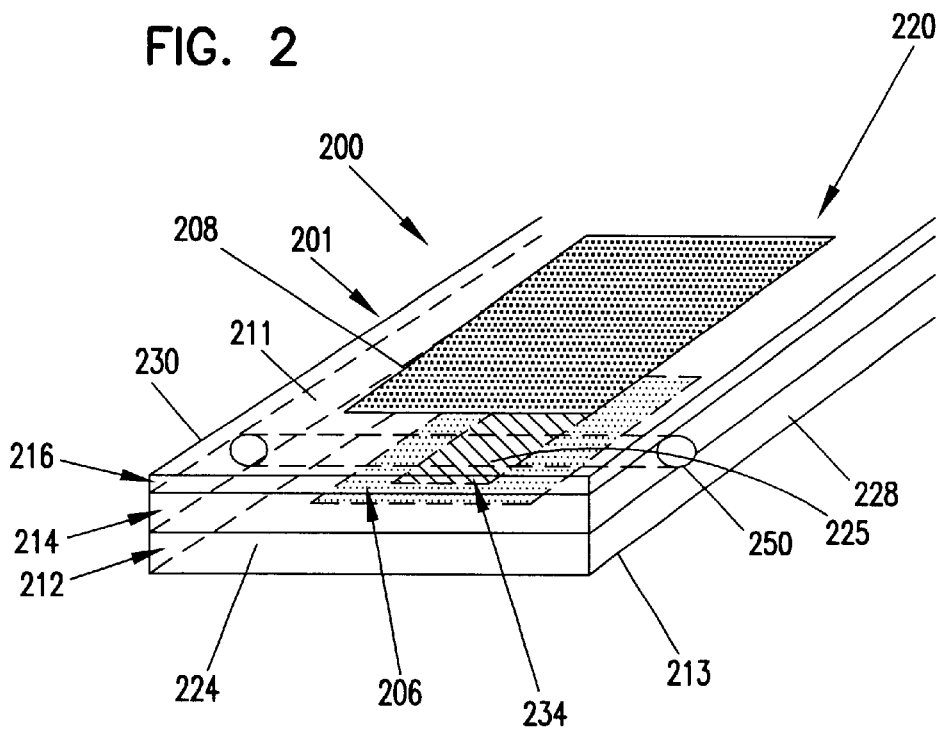
FIG. 2 is a perspective view of an analyte sensor in accordance with another embodiment of the invention.

An alternative embodiment of a sensor 200 is shown in FIG. 2. The sensor 200 includes a sensor body 201 having a top surface 211, a bottom surface 213, side edges 228 and 230, a distal edge 224, and a proximal end 220. The body 201 also includes a working electrode 206, a counter/reference electrode 208, and a sensing layer 234. In this embodiment the working electrode 206 and the sensing layer 234 are still located at an "edge" 225 of the sensor 200, but a channel 250 is formed in the sensor 200 to define an edge 225 that is actually located inside the body of the sensor 200.

The base layer 212 and the top layer 216 are generally the same as those described above. They are separated by a spacer 214 which is adhered, glued or bonded to the top 212 and base layers 216. The spacer and adhesive can be combined into a single layer, for example, by using a double-sided adhesive as a spacer.

A channel 250 is formed in the spacer 214. The channel 250 can pass entirely through the sensor 200, as shown, or have only one opening and pass only part of the way through the sensor. The channel 250 is designed to permit body fluid to pass into the channel 250 and contact the edge 225. The working electrode 206 and the sensing layer 234 are generally the same as those described above and are exposed at the edge 225 such that they can be in contact with fluid at the edge 225 in the channel 250.

The counter and reference electrodes 208 are generally the same as those described above, and may be located at a variety of positions. In addition to those described above, the positions include positions within the channel 250 that are electrically isolated from the working electrode 206.

Figure 3:
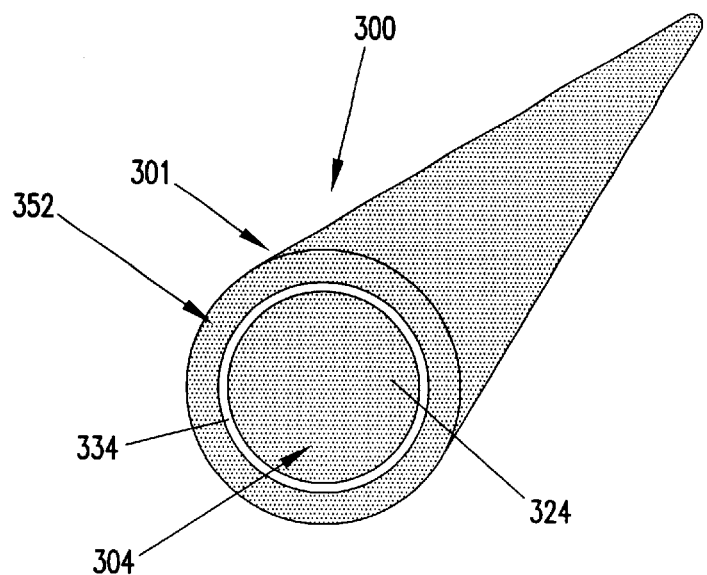
FIG. 3 is a perspective view of an analyte sensor in accordance with another embodiment of the invention.

FIG. 1 and FIG. 2 illustrate embodiments of planar sensors. However, other geometries can also be used. As one example, the topography of the sensor can be curved. As shown in FIG. 3, an example of another embodiment includes a sensor 300 that is cylindrical. The sensor 300 includes a sensor body 301 including an outer layer 352, a sensing layer 334 and a working electrode 304. The sensor body is generally cylindrical in shape and defines a distal front edge 324. In this cylindrical embodiment there is a conductive central rod or wire that serves as the working electrode 304. The sensing layer 334 is coated on the rod or wire 304, and the insulating layer 352 is coated on top of the sensing layer 334. The sensing layer 334 and the insulating layer 352 can be applied in dip or spray coating processes. The sensing layer and working electrode are exposed at the distal edge 324 such that they can come into contact with fluid to be measured when the sensor is inserted. It will be appreciated that a long, continuous rod, wire, or fiber bundle can be formed in such a fashion, and cut into individual sensors.

Figure 4:
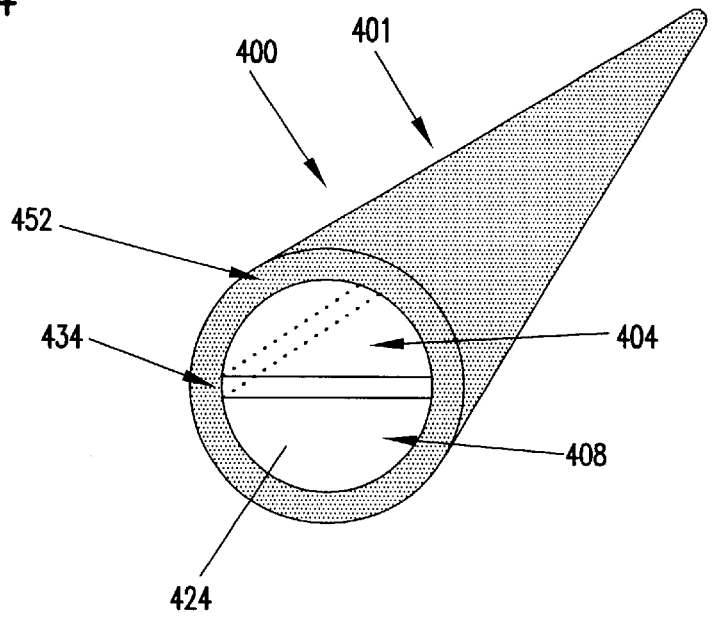
FIG. 4 is a perspective view of an analyte sensor in accordance with another embodiment of the invention.

Yet another embodiment of a sensor 400 of the present invention is illustrated in FIG 4. The sensor 400 includes a sensor body 401 including an outer layer 452, a working electrode 404, a reference electrode 408, and a sensing layer 434. In this embodiment, the working electrode 404, reference electrode 408, and sensing layer 434 are formed in the insulating layer or outer jacket 452. The sensing layer 434, working electrode 404, and reference electrode 408 are exposed at a distal edge 424 of the body. The sensing layer 434 is exposed such that it can come in contact with fluids exposed to the distal edge 424 of the sensor. Such a sensor 400 may be built to very tight tolerances in high volumes with high reproducibility and at a low cost using plastic production methods, such as extrusion molding and injection molding. The working 404 and reference 408 electrodes can be conductive materials or can include plastic or resin which serves to bind conductive materials, such as carbon, gold, platinum, palladium, silver and others known to those skilled in the art. A suitable plastic is styrene elastomer (RTP 2799X66439 black, L.N.P. Plastics, Chicago, Ill). The working electrode 404, counter electrode 408 and outer jacket 452 can be co-extruded using existing techniques. While a cylindrical sensor 400 is illustrated many other geometries are suitable, including planar sensors. Such a sensor can be used either in vivo or in vitro. It can be operated using an amperometric or coulometric method. Such a sensor and production process is suitable, for example, for the in vitro coulometric sensors described in U.S. Pat. No. 6,338,790, "Small Volume In Vitro Analyte Sensor with Diffusible or Non-leachable Redox Mediator," incorporated herein by reference. A particular advantage of such manufacturing processes for such sensors is the ability to provide the very reproducible thin layer cell described in the patent application.

Figure 16:
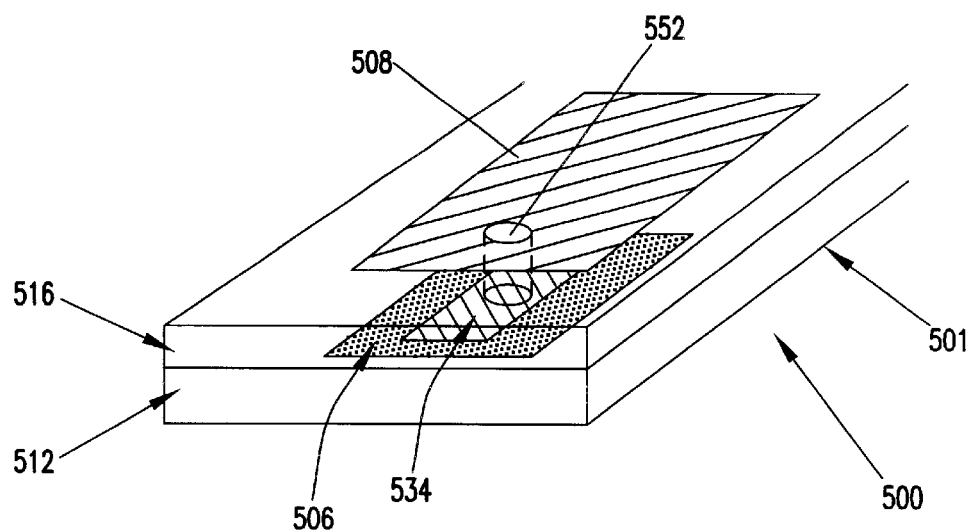
FIG. 16 is a perspective view of an analyte sensor in accordance with another embodiment of the invention.

While the sensors described herein restrict analyte diffusion to the sensing layer from an edge of the sensor, one skilled in the art will recognize that a similar result may be obtained with a sensor in which analyte diffuses from one of the large, planar or curved surfaces. In such embodiments analyte diffusion from a peripheral edge is not required. For example, a small hole, incision or channel can be formed in the body of the sensor to form a non-peripheral edge. For example, referring to FIG. 16, an embodiment of a sensor 500 including a body 501 having a top layer 516 a bottom layer 512, a working electrode 506, a sensing layer 534, and a counter/reference electrode 508 is shown. The sensor body 501 includes a small hole 552 in the top layer 516 to permit analyte diffusion to the sensing layer 534. To eliminate or reduce the need for a mass transport limiting membrane, the hole or incision is typically small enough to restrict mass transport of the analyte to the sensing layer. The hole or incision may be formed by a number of methods, including use of a laser, die cutting, or slitting the surface.

In an embodiment similar to those described above, the hole, incision or channel is formed completely through a portion of the sensor, passing through the top layer and the base layer. In such an embodiment, analyte diffusion to the sensing layer can take place from both sides of the sensor. Diffusion takes place from the hole to the sensing layer via an internal edge of the sensor.

Operation of Sensor

Sensors embodying the invention can operate in the same manner as the sensor described in U.S. Pat. No. 6,175,752. The sensor can be operated in an amperometric or coulometric method and can directly substitute for the sensor described in U.S. Pat. No. 6,175,752. The sensor also operates in the analyte monitoring system described in U.S. Pat. No. 6,175,752.

Manufacturing Process

Sensors embodying the invention can be designed for high-volume manufacturing processes, including both batch processes and continuous processes. In a batch process, the sensors are formed on cards or sheets. In a continuous process, the sensors can be formed on a web with the electrodes being a repeated pattern along the running axis of the web. The sensors are designed to be manufactured using known manufacturing process steps, such as electrode screen printing on the bottom or top layers, nano-scale reagent deposition, coating and curing the top layer, lamination of sheet materials, and cutting of the sensors from the sheets or rolls. The sensors may also be made using extrusion processes. The sensors can be made using manufacturing techniques described in U.S. patent application Ser. No. 09/034,422 and in U.S. Pat. No. 6,338,790, both of which are incorporated herein by reference.

One example of a suitable sensor configuration is made by screen printing a carbon ink on the front side of a plastic sheet, and a silver/silver chloride counter-reference electrode on the back of the sheet. The sensing layer formulation is striped onto the carbon electrode providing widths less than 0.40 mm×16 milx, and lengths less than 0.75 mm×30 milx. High percent solids formulations, 10–30 wt. %, are preferred so that adequate thicknesses can be achieved from a single application. A biocompatible coating, for example a silicone sealant, a pressure sensitive adhesive, or a polyurethane coating, is used to encapsulate the carbon ink and sensing layer. Preferably, the urethanes are materials are hydrophobic (non-swellable) and amorphous (low content of crystalline regions, hard segments). Such materials provide good adhesion to the substrate. The moisture cured polypropylene oxide or glycol urethanes are preferred. Some other examples of polyurethanes include those commercially available under the following names: LORD 2941 and LORD 2940. Additionally moisture curable polyurethanes named BAYTEC MP-120, (diphenylmethane diisocyanate (MDI)-terminated polyether (polypropylene glycol) prepolymer) and BAYTEC MP030, both commercially available from Bayer, are also suitable.

After curing the biocompatible coating, the sensing layer is exposed by slitting the tip of the sensor to reveal the edge. Connections are made to the silver/silver chloride and carbon electrodes in a variety of ways; some embodiments encapsulate the connection to aeliminate or reduce the occurrence or magnitude of corrosion currents.

The individual sensors can be cut from the card, sheet or web by a steel die or comparable process. The die cuts are made such that the cut profile remains substantially outside the perimeter of the working electrode pattern on all sides except for the region of the sensing layer. In this region the cut crosses the working electrode, thus exposing a cross-section of all the layers described above. This cut region becomes the analyte-sensing region of the sensor. Other cutting processes are suitable, such as slitting or kiss-cutting. The preferred method is slitting because fewer particulates are formed in a slitting operation compared to a die cutting process.

Embodiments of the sensors described herein can have one or more of the following advantages over previous implantable analyte sensors:

1. The sensor geometry inherently limits the mass transport of analyte to the sensing layer, thereby eliminating the need for a mass transport limiting membrane. The sensor's linear range is wide even without a mass transport limiting membrane.
2. The sensor is easily manufactured using standard, existing methods for electrode printing, reagent deposition, lamination, and slitting. In particular, the need to reliably attach a mass transport limiting membrane with reproducible analyte mass transport characteristics to the surface of an electrode can be eliminated.
3. The operational stability and hence operational life of the sensor can be enhanced.
   Some of the reasons for the enhancement can include:
   A. The reduced flux of analyte (e.g., glucose) to the sensing layer reduces the rate of enzyme turnover, thereby extending the life of the enzyme.
   B. As enzyme at the edge of the sensing layer is deactivated during use, glucose diffuses deeper into the sensing layer to reach relatively unused enzyme, thereby extending the life of the sensor.
   C. The immobilization of the sensing layer between the base and top layers stabilizes the sensing layer, thereby extending the life of the sensor.
   D. The immobilization of the sensing layer between the base and top layers limits the swelling of the hydrogel, reduces the probability that portions of the sensing layer that are distant from the working electrode will not be in electrical communication with the working electrode, and reduces the risk of poorly bound sensing hydrogel being lost into the environment.
4. The risk of enzyme or mediator leaching into tissue is reduced.
5. Sensor materials can be selected to permit the diffusion of appropriate amounts of different reactants to the sensing layer, even when they are present in 10 or 100-fold different concentrations in the body. An example is diffusion of glucose from the edge and diffusion of oxygen from the top and edge in an oxygen or peroxide-detecting glucose sensor. Similarly, the sensor materials can be chosen to permit the necessary levels of transport of reaction products away from the sensing layer.

Sensor Engineering

The sensitivity of the sensor is determined by a number of factors that may be controlled in the design of the sensor, including: (i) the surface area (length and height) of the exposed edge; (ii) the length of the analyte diffusion path in the sensor; and (iii) the diffusion coefficient of the analyte in the diffusion path and in the sensing layer.

The following is an analysis of the conditions for signal stability for a defined glucose concentration range for the sensor 100 shown in FIG. 1. The height of the solution-exposed face of the analyte-responsive region of the sensor is h and its length is L. In the case of the sensor 100 shown in FIG. 1 and where the sensing layer 134 is a glucose oxidase/redox polymer layer on a printed carbon electrode that has at least the same length as the sensing layer, h represents the thickness of the sensing layer and L represents its length. The condition for signal (current output) stability is complete electrooxidation of glucose-flux by the working electrode 104. At a solution concentration $C_{sol}$ (moles/cm$^3$), this flux is $D_{sol} \times h \times L \times C_{sol}$, where $D_{sol}$ (cm$^2$/sec) is the diffusivity (diffusion coefficient) of glucose in the assayed solution. Glucose diffuses into the face with a diffusivity of $D_{film}$ (cm$^2$/sec). It is electrooxidized on the face in a reaction the rate constant of which is k (moles/cm$^2$), when the reaction is controlled by the kinetics of one of the reaction steps, not by glucose transport. The amount of glucose reacted is thus proportional to $D_{film} \times k$, yielding the condition for a stable signal:

$$D_{sol} \times h \times L \times C_{sol} < a \times D_{film} \times k \times L \quad (1)$$

where a is a constant, or simply:

$$D_{sol} \times h \times C_{sol} < a \times D_{film} \times k \quad (2)$$

Because the absolute signal is proportional to L, its magnitude can be tailored to the electronic requirements of the system.

The stabilities of redox polymer- enzyme biosensors are largely limited by the effective enzyme lifetime, assuming sufficient optimization of the redox polymer chemistry. The advantage of the inventive sensor design is continued sensor performance with the occurrence of decreased enzyme activity. Enzymatic conversion of the analyte occurs further up the channel as the enzyme at the tip of the sensor loses activity. The inventive sensor design provides improved stability over traditional open-face biosensors because 1) glucose diffusion is restricted to the edge of the sensing layer, increasing enzyme lifetime, and 2) any enzyme deactivation is compensated by further diffusion of the analyte up the sensor channel to regions of the sensing layer with sufficient enzyme activity.

Upon making the sensing layer thin, the structural stress resulting from sensing layer swelling is reduced. A sensing layer less than 100 μm thickness is suitable, and 1–10 μm thickness is preferred.

If the sensing layer includes a water-swollen gel then an elastically deforming top layer is preferred, to accommodate structural stress in the sensor created by the swelling gel. A suitable material is an elastomeric overcoating.

Use of a sensing layer characterized by a high $D_{film}$ is desirable. A suitable sensing layer is a hydrogel in which glucose diffuses nearly as rapidly as in water. Nevertheless, it is desirable to cross link the gel to prevent extraction of the gel constituents, as long as $D_{film}$ is not drastically reduced. Reduction of $D_{film}$ can lead to increased signal contributions from interferants, as well as worsened current stability.

In some sensing layers oxygen is not required as a reactant, and variations in oxygen concentration can lead to measurement errors. For example, in some cases oxygen can oxidize electron transport mediators, thereby interfering with their ability to carry charge to an electrode. In such cases it is desirable to minimize the dissolved oxygen present in the sensing layer by using a top layer material that is not very permeable or is impermeable to oxygen. Most elastomeric top layers are highly permeable to oxygen, but oxygen impermeable elastomers can be selected. Alternatively, oxygen access can be blocked by placing a chlorided silver foil counter-reference electrode on the top layer.

Sensing Layer Composition

Suitable sensing layers for sensors embodying the invention typically include three major components: 1) redox polymer, 2) enzyme, and 3) crosslinker. In addition, other components can be present such as, for example, enzyme stabilizers, processing aids, plasticizers, and humectants. Examples of stabilizers include glutamate, gluconate, proteins, zinc salts, calcium salts, polyethylene glycol, and a variety of other materials such as buffers. Processing aids include, for example, viscosity modifiers used to facilitate the sensing layer deposition, materials to improve the drying characteristics, or surfactants used to improve wetting of the substrate. Humectants and plasticizers, such as glycerol, can be used to maintain the sensing layer gel in a swollen state during application of the top layer. This can reduce mechanical stresses in the sensing layer during actual use if the sensing layer exchanges the plasticizer for water, and there is little change in volume.

One useful redox polymer for a glucose sensor is prepared from polyvinyl pyridine (160K) by first quaternizing 15% of the pyridine finctionalities with bromohexanoic acid, then converting all the pendant carboxylic acid functionality into amides by reacting with an amide-containing redox mediator, such as, for example, (4-(6-aminohexyl)amino-2, 2'bipyridine)bis(1,1'-dimethyl-2,2'-biimidazole)osmium. (III) trichloride. Another useful redox polymer is formed by complexing $(Os(bpy)_2Cl)_{+/2+}$ with polyvinyl pyridine. The redox polymer comprises 20 to 80 wt. % of the formulation solids.

Suitable crosslinkers for polyvinylpyridine redox polymers include multifunctional epoxides such as poly(ethylene glycol) 400 diglycidylether from Polysciences, N,N-diglycidyl-4-glycidyloxyaniline from Aldrich Chemical Co. (Milwaukee, Wis.), diglycidyl 1,2-cyclohexanedicarboxylate from Aldrich, and other multifunctional epoxides. The crosslinker is typically 5 to 50 wt. % of the formulation solids. The enzyme component, glucose oxidase, is typically 5 to 60 wt. % of the formulation solids.

The above description provides a basis for understanding the broad meets and bounds of the invention. The following examples and test data provide an understanding of certain specific embodiments of the invention. The invention will be further described by reference to the following detailed examples. These examples are not meant to limit the scope of the invention that has been set forth in the claims. Variation within the concepts of the invention are apparent to those skilled in the art.

EXAMPLES

Example 1

A glucose sensor with key elements similar to those shown in FIGS. 1 and 2 was designed and constructed. The working electrode and sensing layer were formed in a manner very similar to that shown in FIG. 1, but the working electrode and sensing layer were slightly recessed from the distal tip of the sensor. Glucose diffused from the solution to the distal tip and into the recessed working electrode. The Ag/AgCl counter/reference electrode was located in a sandwiched channel, very similar to the channel shown in FIG. 2.

The sensor was constructed as follows. A piece of polyester approximately 150 $\mu$m thick was printed with Ercon G449 graphite ink (Ercon, Inc., Wareham, Mass.) to a trace width of approximately 750 $\mu$m and an ink thickness of about 12 $\mu$m. The polyester was cut to a width of approximately 3 mm so that the ink trace was centered. Enzyme/redox polymer sensing chemistry was applied to the distal end of the carbon trace as three 0.1 $\mu$L drops, allowing the drops to dry before the addition of the next drop. During the coating the sensing layer extended beyond the width of the carbon trace. The coated assembly was cut with a sharp blade perpendicular to the carbon trace to expose a sensing layer portion free from drying edge effects.

A mating top half of the device was constructed from the same polyester but coated with silver/silver-chloride ink (Ercon R414) to serve as the counter-reference. This ink was patterned similarly to the graphite except that the length of the trace was shorter by about 2 mm and ended in a rectangular "paddle". The silver face was then covered with 3M 467 pressure sensitive adhesive (3M Co., St. Paul, Minn.) everywhere to about 25 $\mu$m thick except for a connection surface at the proximal end of the device and a channel of about 1.25 mm width over the silver paddle and perpendicular to the long axis of the trace. This channel served to allow fluid communication with the electrode, and the adhesive at the distal end of the piece after the channel served to seal the sensing layer from fluid penetration except from the cut edge.

The two halves were joined together by hand pressure so that the sensing layer was covered by adhesive except for the cut edge; fluid could travel into the channel to make contact with the reference electrode but did not communicate with the sensing layer. The chemistry of the sensing layer included $[Os(bpy)_2Cl]_{+/2+}$ complexed with poly-4-vinyl pyridine (10 mg/ml in 30% ethanol/70% HEPES buffer 10mM pH 8.0), where bpy is 2,2'-bipyridine, glucose oxidase (10 mg/ml in HEPES buffer 10 mM pH 8.0) and poly (ethylene glycol) diglycidyl ether (400 MW 2.5 mg/ml in water). The sensing layer was allowed to cure at 20° C., 50% relative humidity for 20 hours.

Four sensors were constructes as above, and were operated in phosphate buffered saline, 20 mM phosphate, 100 mM chloride, pH 7.1 at 10 mM glucose for a period of 23 hours. Calibration data was taken before and after the 23 hour operation of each of the four sensors.

Figure 5:
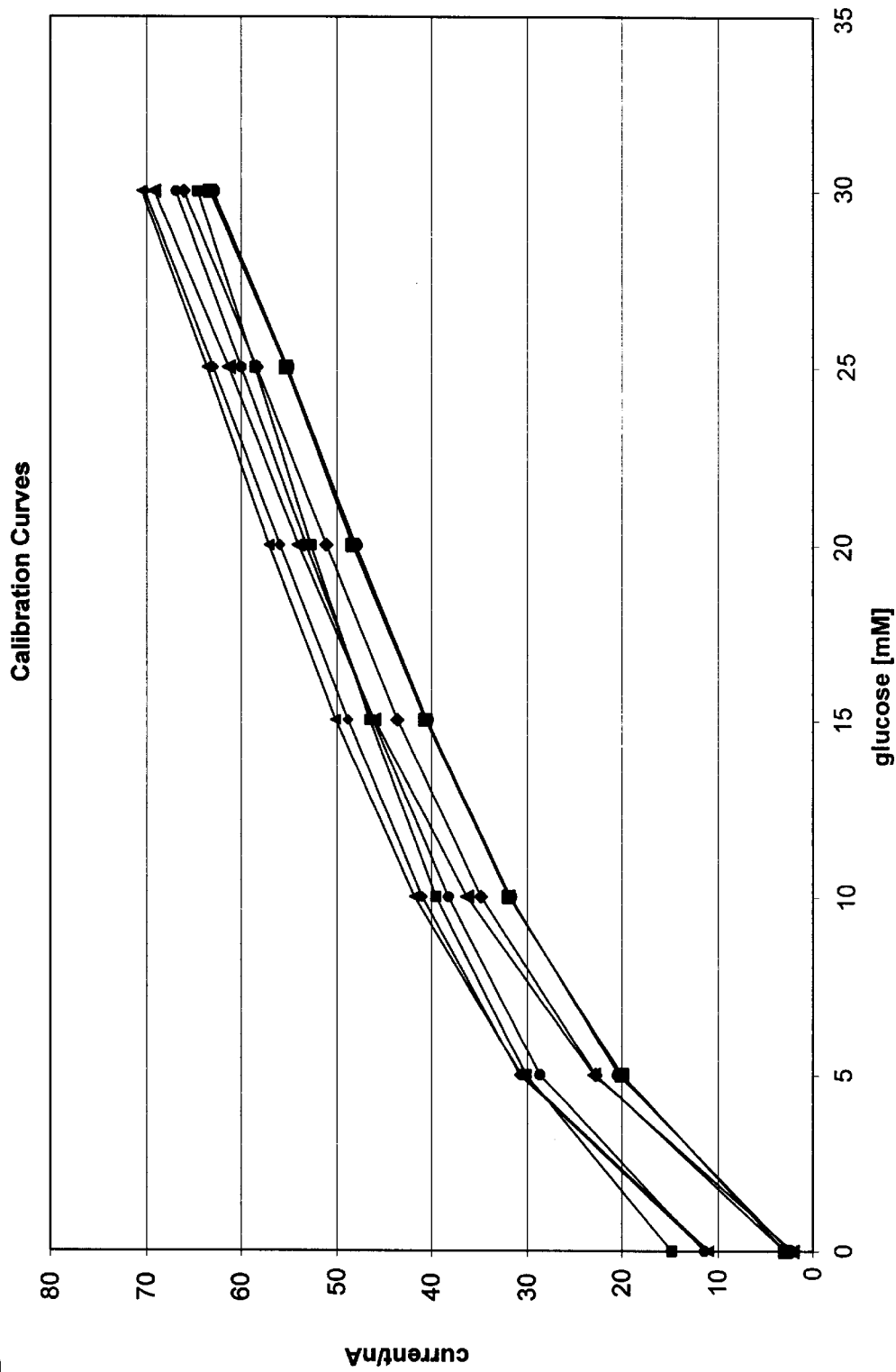
FIG. 5 shows a calibration curve of the sensors of Example 1, before and after the 23 hour operation of the sensors.

FIG. 5 shows the calibration curve of the four sensors before and after the 23 hour operation of the sensor, wherein the diamond symbols indicate the first sensor, the squares indicate the second sensor, the triangles indicate the third sensor, and the circles indicate the fourth sensor. Additionally, the solid symbols indicate pre-operation calibration data and the hollow symbols indicate post-operation data. As shown, the sensors are highly stable, losing less than about 7 nA of signal across the glucose concentration range during the test. The sensor response is also linear from 5–30 mM glucose, without a mass transport limiting membrane. Sensitivity is very good, at about 2.5 nA/mM glucose in the 7.5 to 30 mM glucose range.

Figure 6:
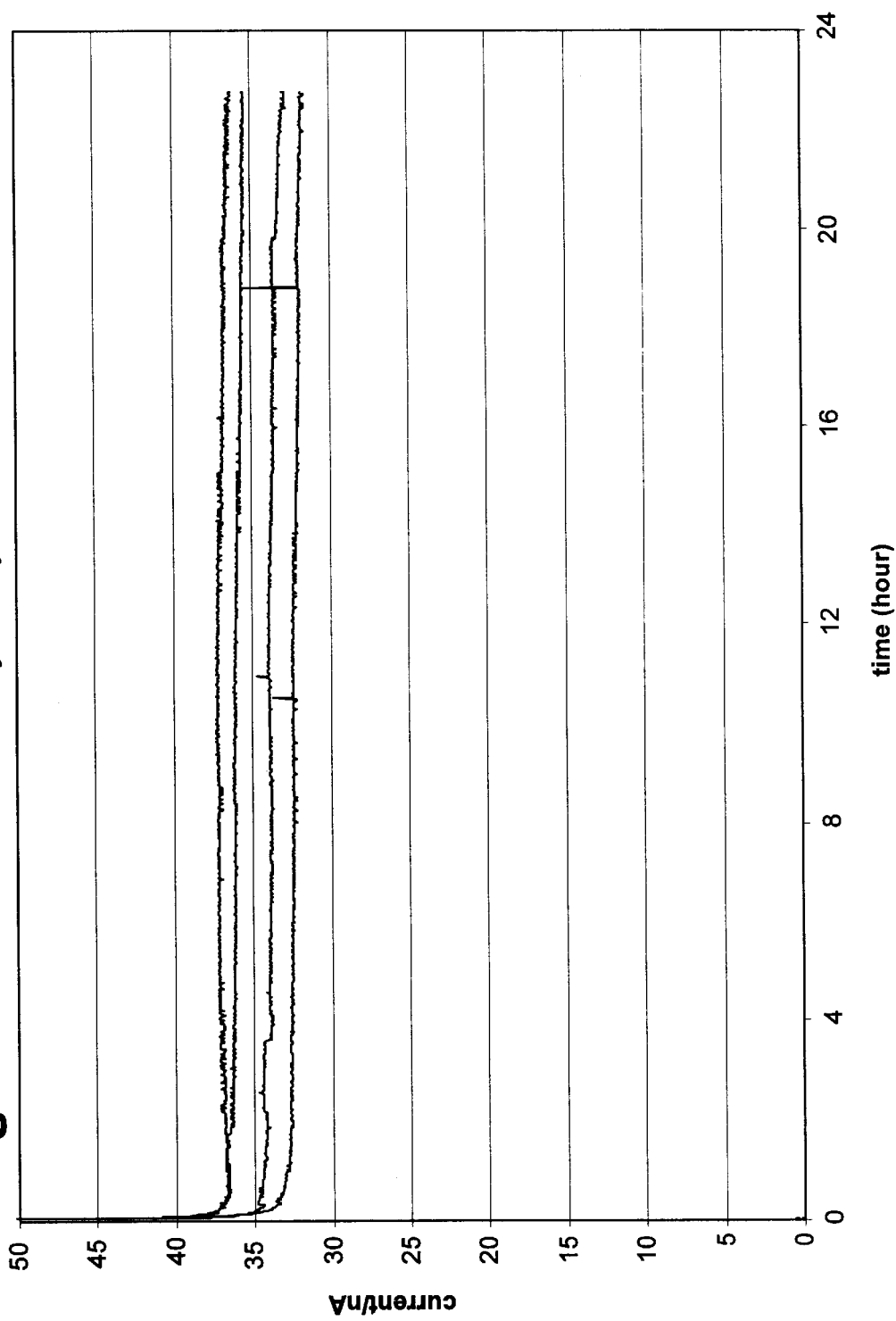
FIG. 6 show a graph indicating the one day stability of the sensors of Example 1.

FIG. 6 provides another illustration of the stability of the sensors during the test. Each of the four lines on this graph corresponds to signal data from one of the four sensors during operation. In each of the sensors, the current decayed rapidly within the first 15 minutes to a stable signal. Signal decay over the 23 hour test period ranged from 0.91% to 5.02%, or an average rate of 0.16% per hour.

Example 2

The glucose sensor illustrated in FIG. 1 was prepared by printing graphite ink onto a polyester substrate, applying the sensing chemistry, then coating urethane encapsulant over the dried sensing layer. A separate Ag/AgCl reference electrode was used as the counter electrode.

A piece of polyester was printed with ERCON G449 graphite ink (ERCON, Inc., Wareham, Mass.) to a trace width of approximately 750 microns and a thickness of 12 microns. The enzyme/redox polymer sensing chemistry was applied as a single 4 nL droplet to the distal end of the sensor and dried at 53° C. for 40 seconds.

The sensor was placed in an environmental chamber maintained at 80% RH (relative humidity) and 25° C. for 24 hours. A moisture-curable urethane prepolymer was coated at 80%RH and 25° C. over the electrodes and sensing layer using a 2 ½ wire wound rod. The urethane was cured after 12 hours at the elevated humidity. After cure, the sensing layer was exposed by slitting through the center of the sensing layer droplet using a rotary die. The finished sensor was die cut from the remaining plastic sheet to provide a total sensor width of 35 thousandths of an inch.

The urethane prepolymer was prepared by mixing together 14.65 g Polypropylene glycol-tolylene-2,4-diisocyanate terminated (8.4% isocyanate) from Aldrich (Milwaukee, Wis.) and 3.54 g Polypropylene glycol bis (aminopropyl ether) ($M_n$=4000) from Aldrich (Milwaukee, Wis.).

The enzyme/redox polymer coating was a 15 wt. % solids where the solids were composed of 34.1 wt. % redox polymer X5 (described below), 41.1 wt. % glucose oxidase GLO-201 from Toyobo Co., Osaka, Japan, and 24.8 wt. % Poly(ethylene glycol) 400 diglycidylether (PEG-400-DGE) from Polysciences, Inc. (Warrington, Penn.). The coating solution was prepared in dilute HEPES buffer. The redox polymer X5 was prepared from Polyvinyl pyridine (160K) by first quaternizing 15% of the pyridine functionality with bromohexanoic acid, then converting all of the pendant carboxylic acid functionality into an amide by reacting with the redox mediator, (4-(6-aminohexyl) amino-2,2'-bipyridine) bis (1,1'-dimethyl-2,2'-biimidazole)osmium (III) trichloride.

Figure 7:
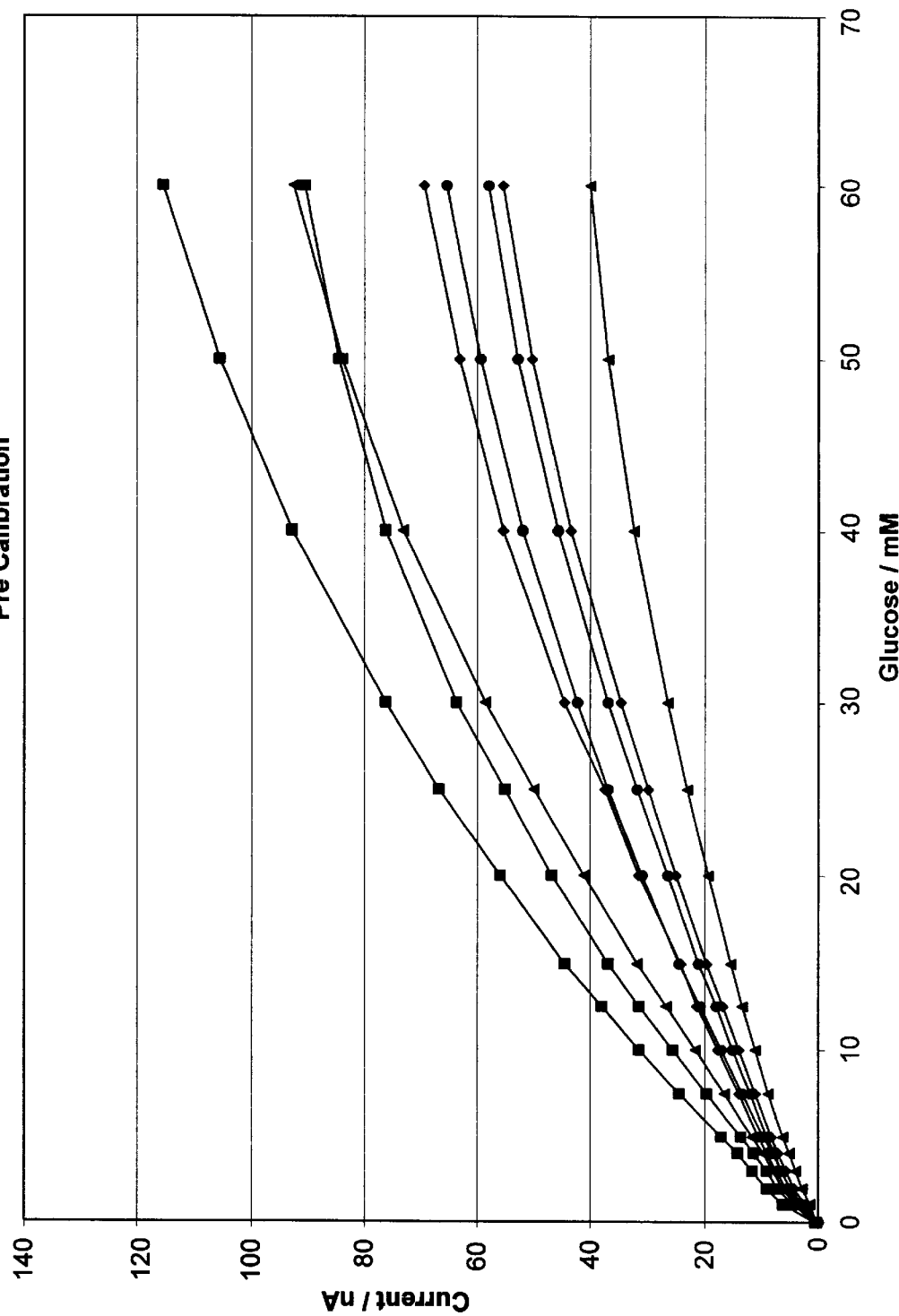
FIG. 7 shows a calibration curve of the sensor of Example 2, before the 43 hour operation of the sensors.
Figure 8:
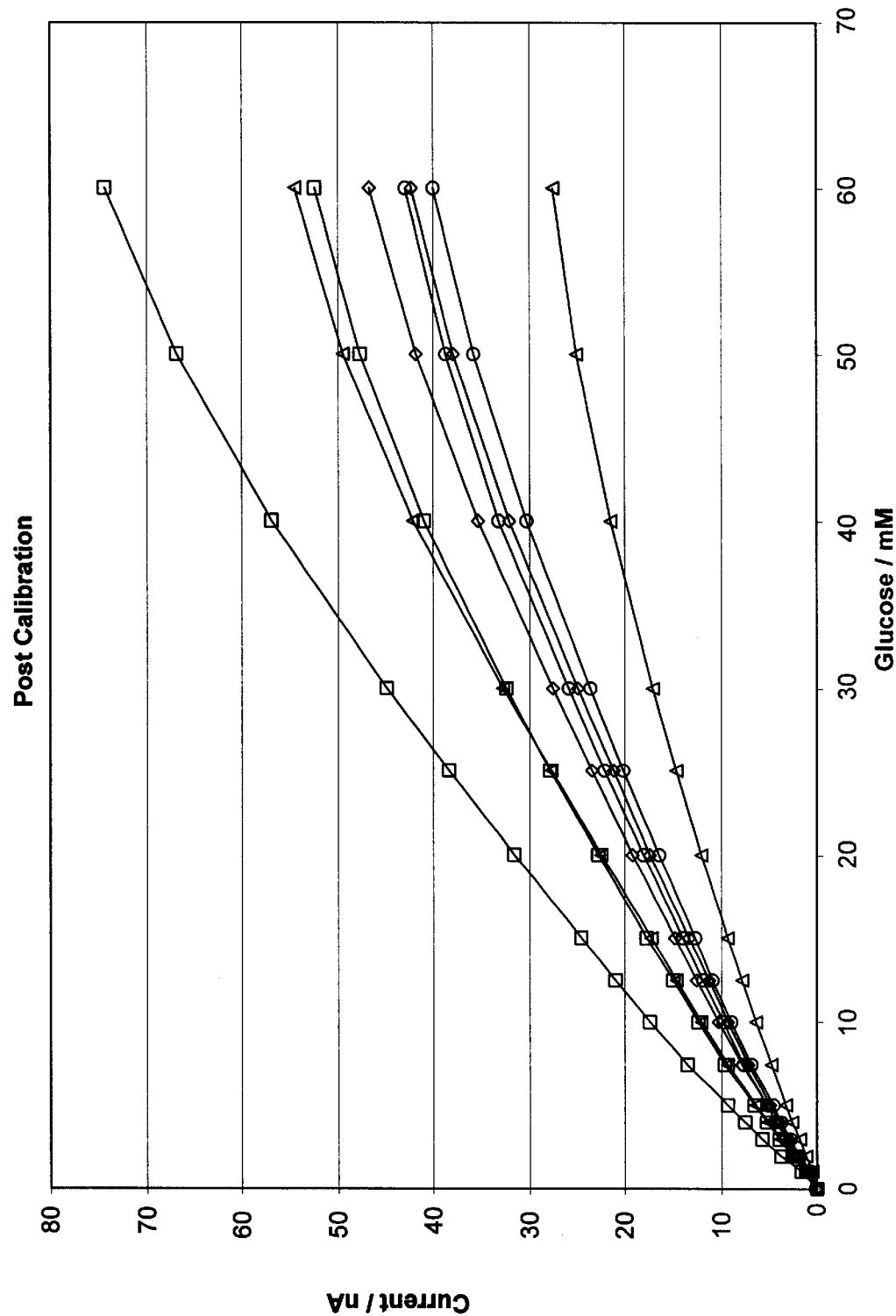
FIG. 8 shows a calibration curve of the sensors of Example 2, after the 43 hour operation of the sensors.
Figure 9:
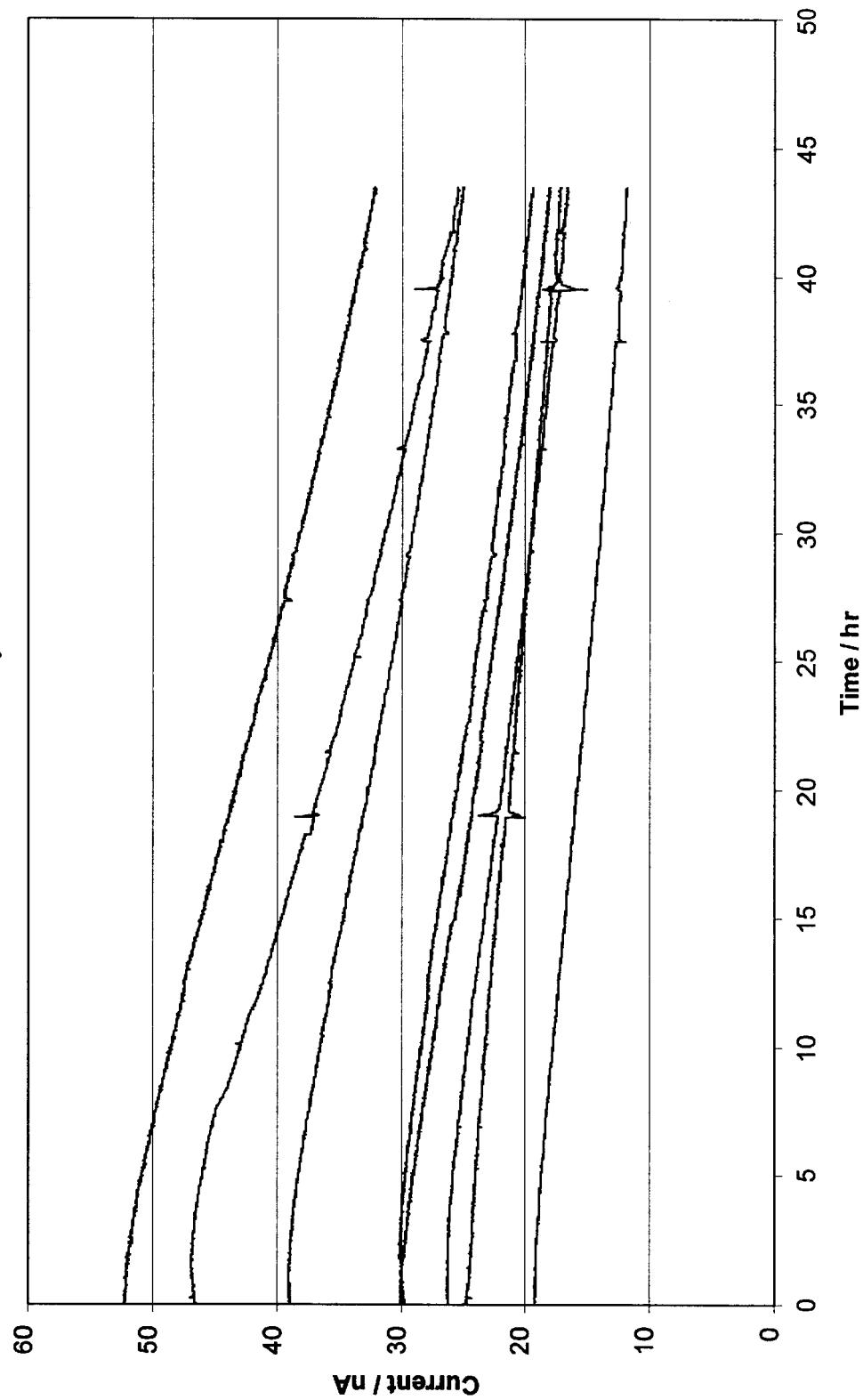
FIG. 9 shows a graph indicating the decline in signal of the sensors during the 43 hour experiment of Example 2.

Eight sensors were constructed as above, and were operated in phosphate buffered saline, 20 mM phosphate, 100 mM chloride, pH 7.1, at 20 mM glucose for 43 hours. Calibration data was taken before and after the 43 hour operation of each of the eight sensors. FIG. 7 shows the calibration curve for each of the sensors before the 43 hour operation, and FIG. 8 shows the calibration curve for each of the sensors after the 43 hour operation. The sensors demonstrated acceptable stability and were sensitive even at higher glucose concentrations. Sensitivity was excellent, about 1–3 nA/mM glucose in the 5 to 30 mM glucose range. FIG. 9 shows the decline in signal of each of the eight sensors during the 43 hour experiment. The decay rate averaged 0.87 %/hour.

Example 3

Figure 10:
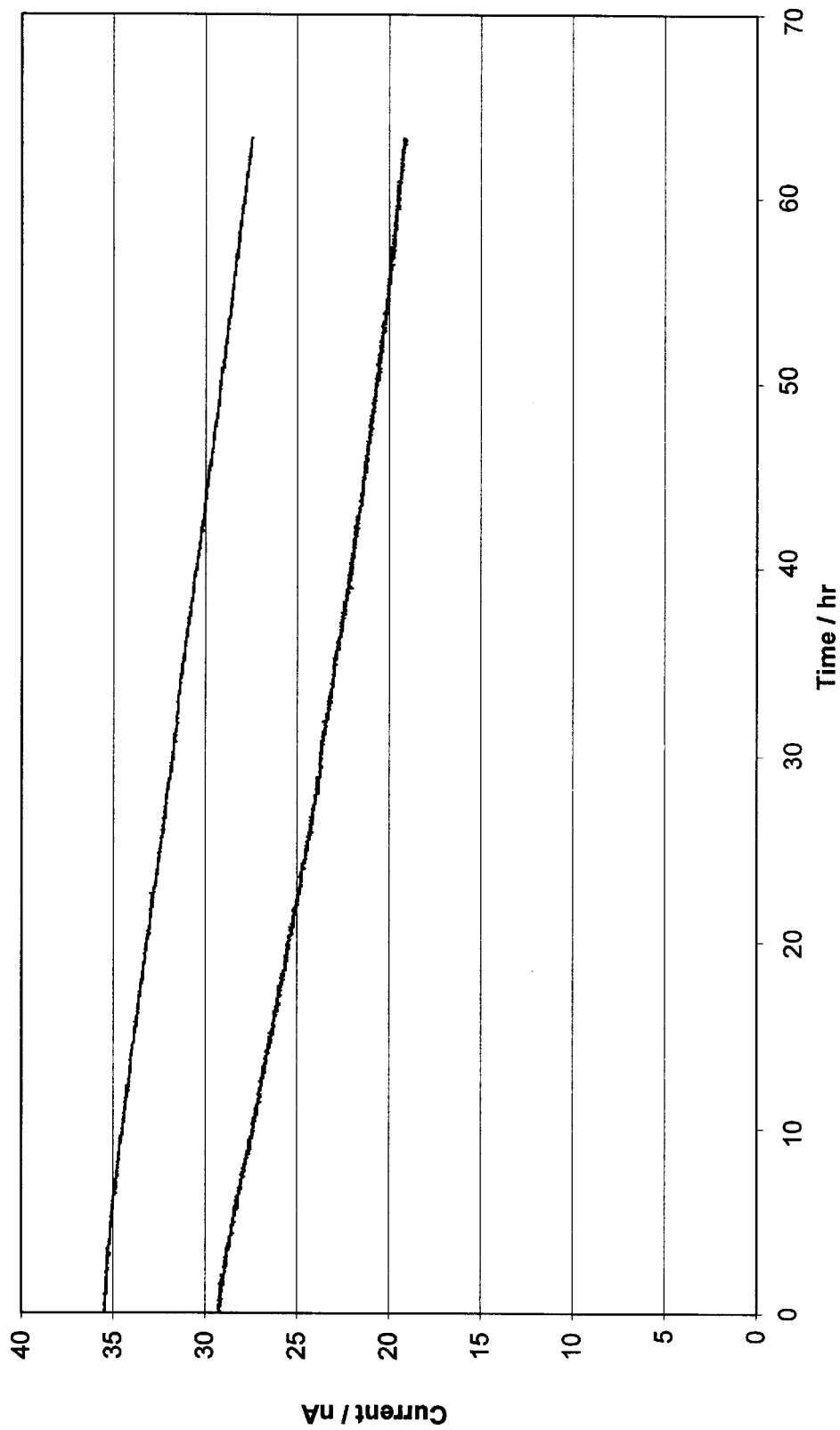
FIG. 10 shows a graph indicating the decline in signal of the sensors during the experiment of Examples 3 and 4.
Figure 11:
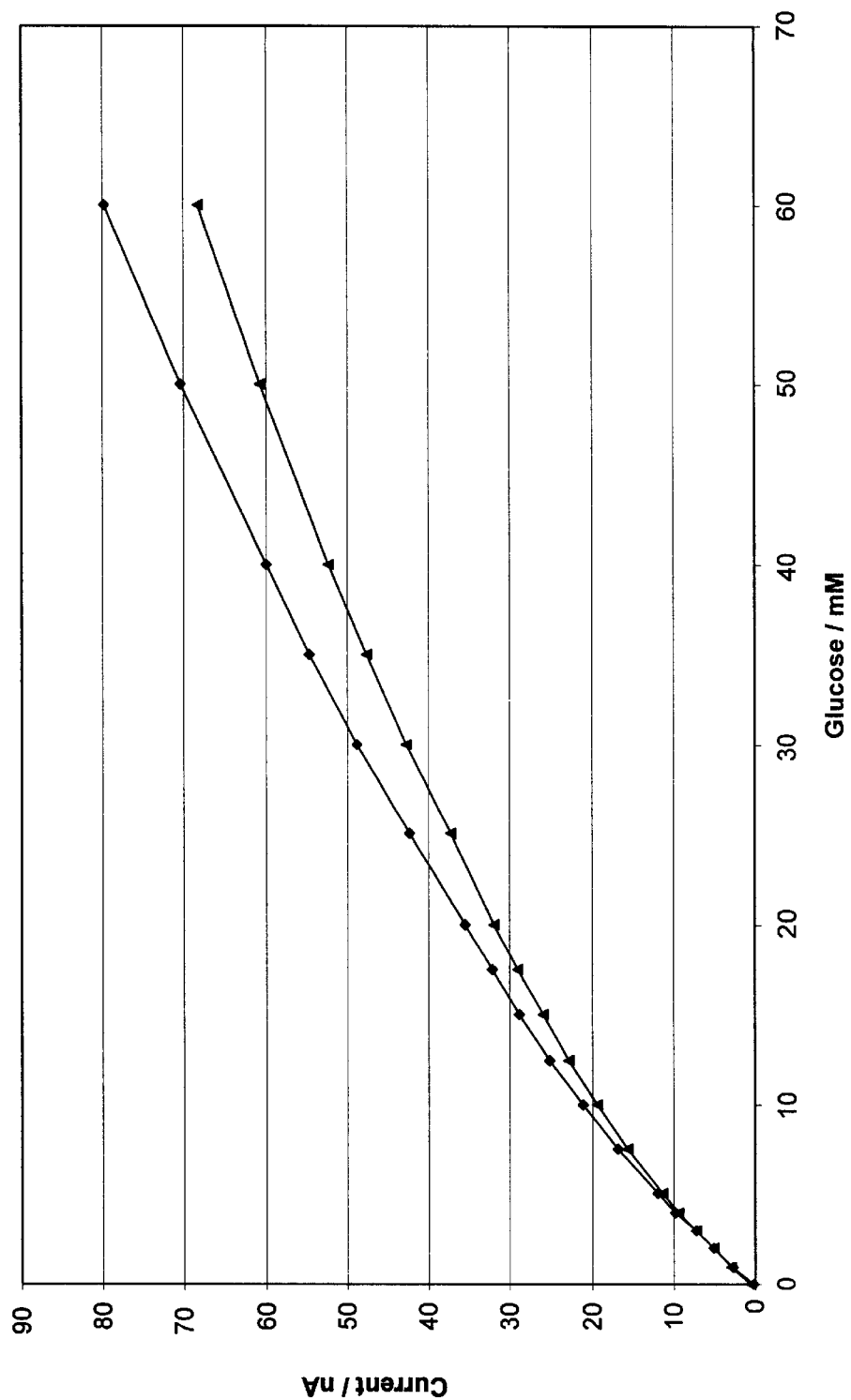
FIG. 11 shows a calibration curve of the sensors of Example 3 and 4, before the stability experiments of Examples 3 and 4.
Figure 12:
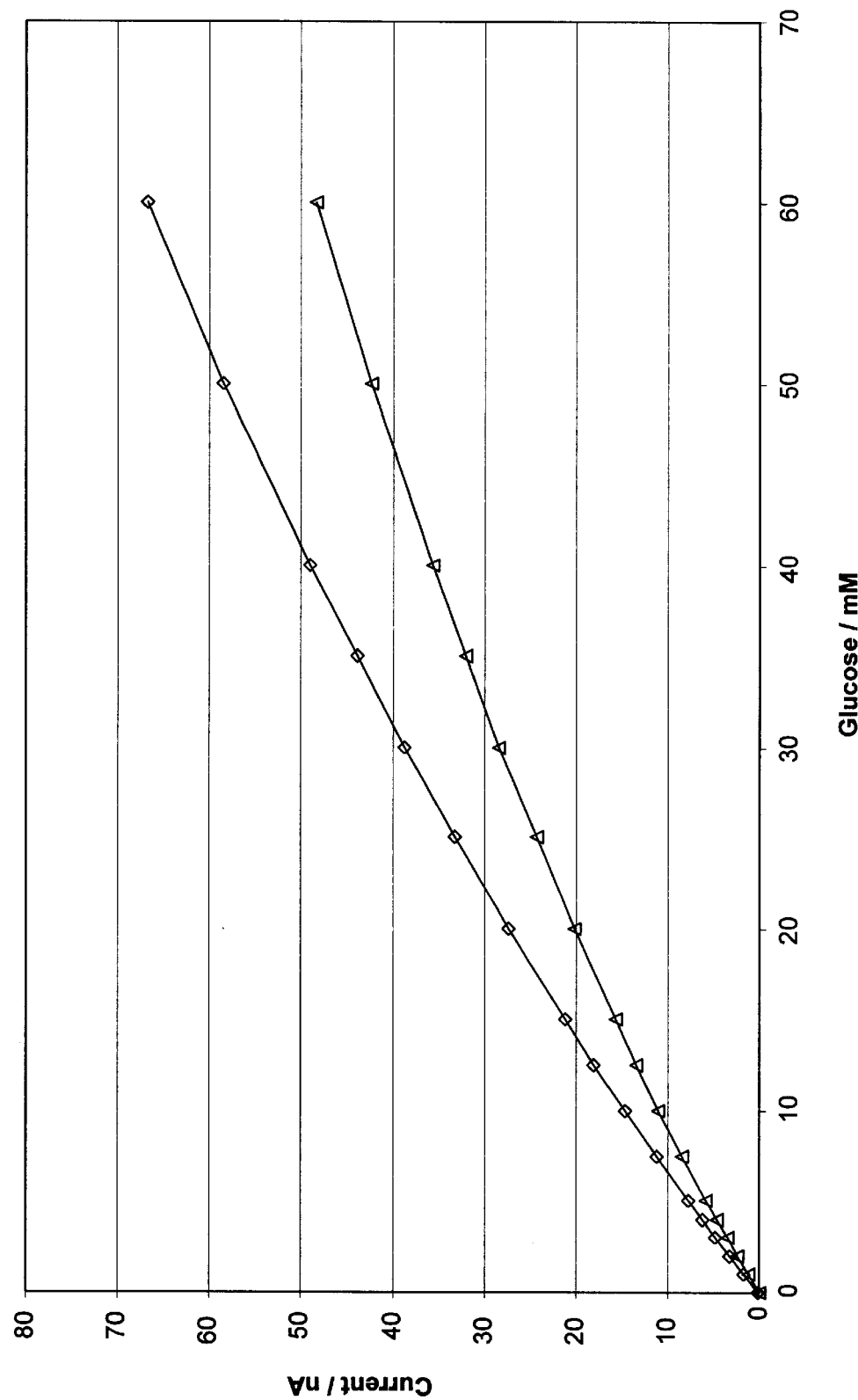
FIG. 12 shows a calibration curve of the sensors of Example 3 and 4, after the stability experiments of Examples 3 and 4.

The electrode preparation procedure from Example 2 was repeated to make a sensor for this example, except the sensing layer was composed of 52.3 wt. % X5, 12.3 wt. % glucose oxidase, 35.4 wt. % PEG-400-DGE at 15 wt. % solids in dilute HEPES buffer 40 nL of the solution was applied to each sensor trace, and then dried at ambient conditions. The urethane was cured at ambient conditions. The results shown in FIG. 10 indicate that the current declined at an average rate equal to 0.35% /hour over the 64 hour stability study. The calibration data collected before and after the stability experiment, shown in FIGS. 11 and 12, indicate a comparable loss of current with good sensitivity extending to high glucose concentrations. The curve marked with the diamonds in FIGS. 11 and 12 represent the data from the sensor in this example.

Example 4

The procedure from Example 2 was repeated to produce a sensor for this example, except that the sensing layer was composed of 66.6 wt. % X5, 13.45 wt. % glucose oxidase, and 20 wt. % PEG-400-DGE at 11 wt. % solids in dilute HEPES buffer. 16 nL of the solution was coated onto each sensor trace and dried at ambient conditions. The urethane was coated and cured at ambient humidity. The results shown in FIG. 10 indicate that the current declined at an average rate equal to 0.53% /hour over the 64 hour stability study. The calibration data collected before and after the stability experiment, shown in FIGS. 11 and 12, indicate a comparable loss of current with good sensitivity extending to high glucose concentrations. The curve marked with the triangles in FIGS. 11 and 12 represent the data from the sensor in this example.

Example 5

Figure 13:
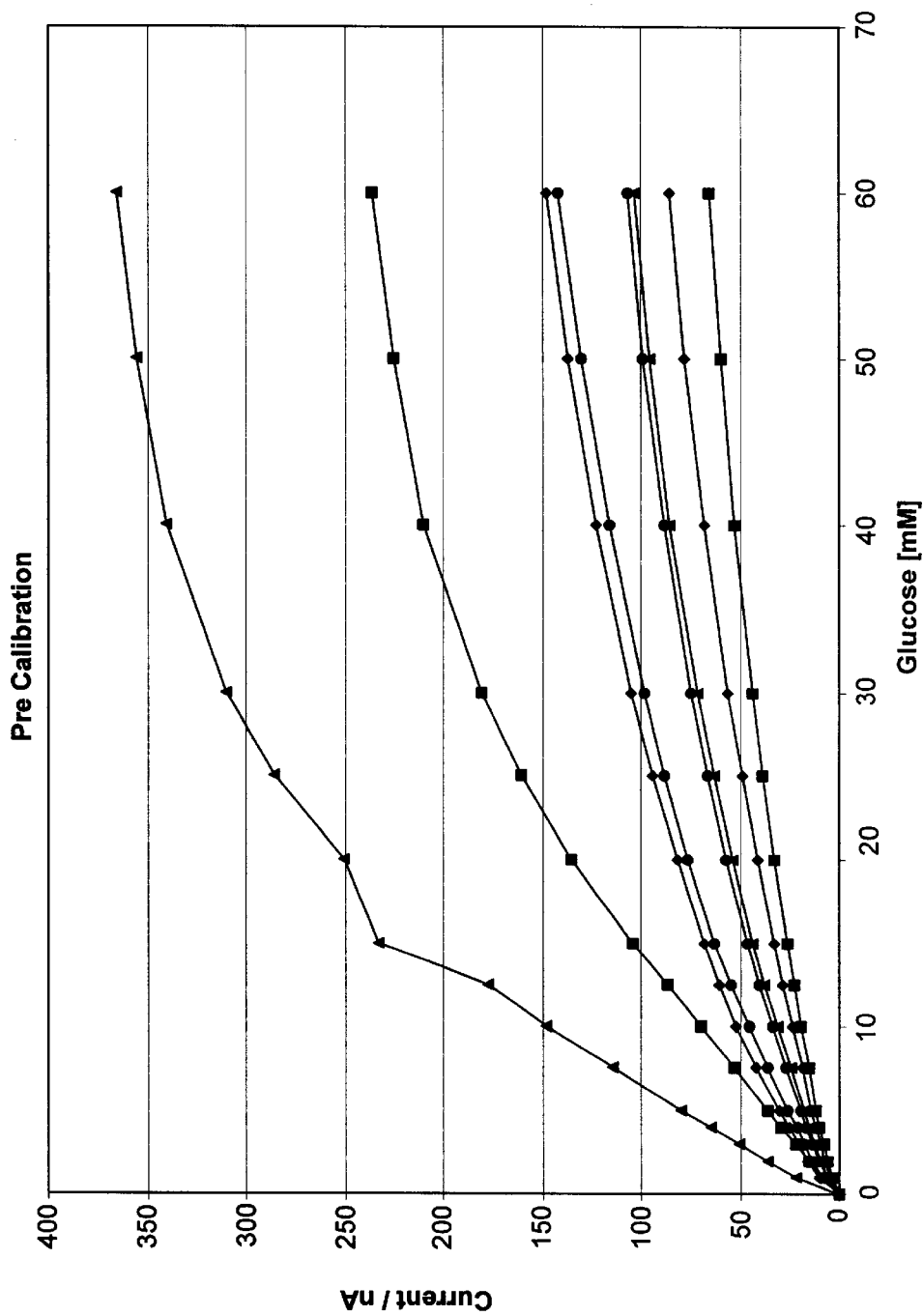
FIG. 13 shows a calibration curve of the sensors of Example 5, before the stability experiments of Examples 5.
Figure 14:
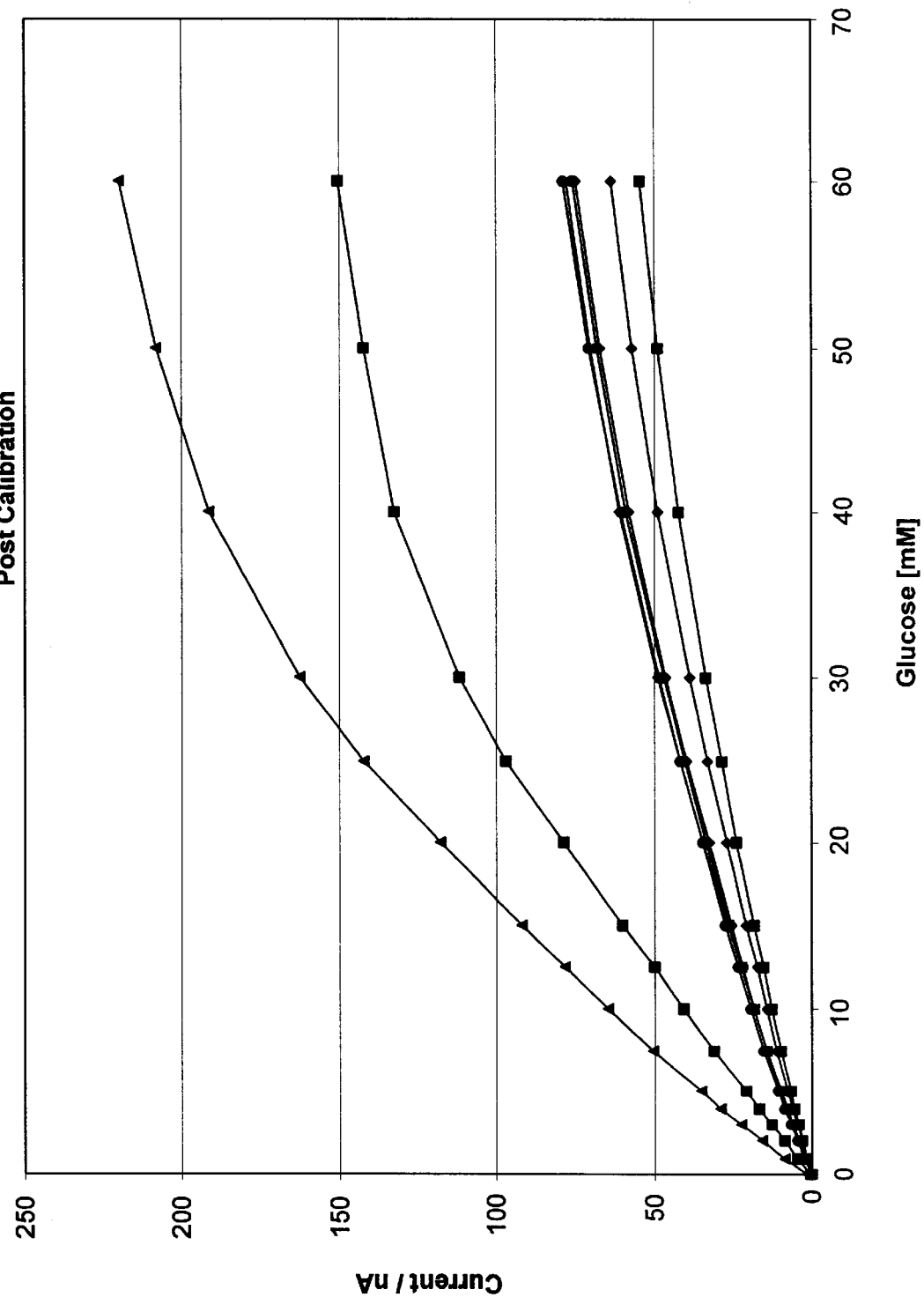
FIG. 14 shows a calibration curve of the sensors of Example 5, after the stability experiments of Examples 5.
Figure 15:
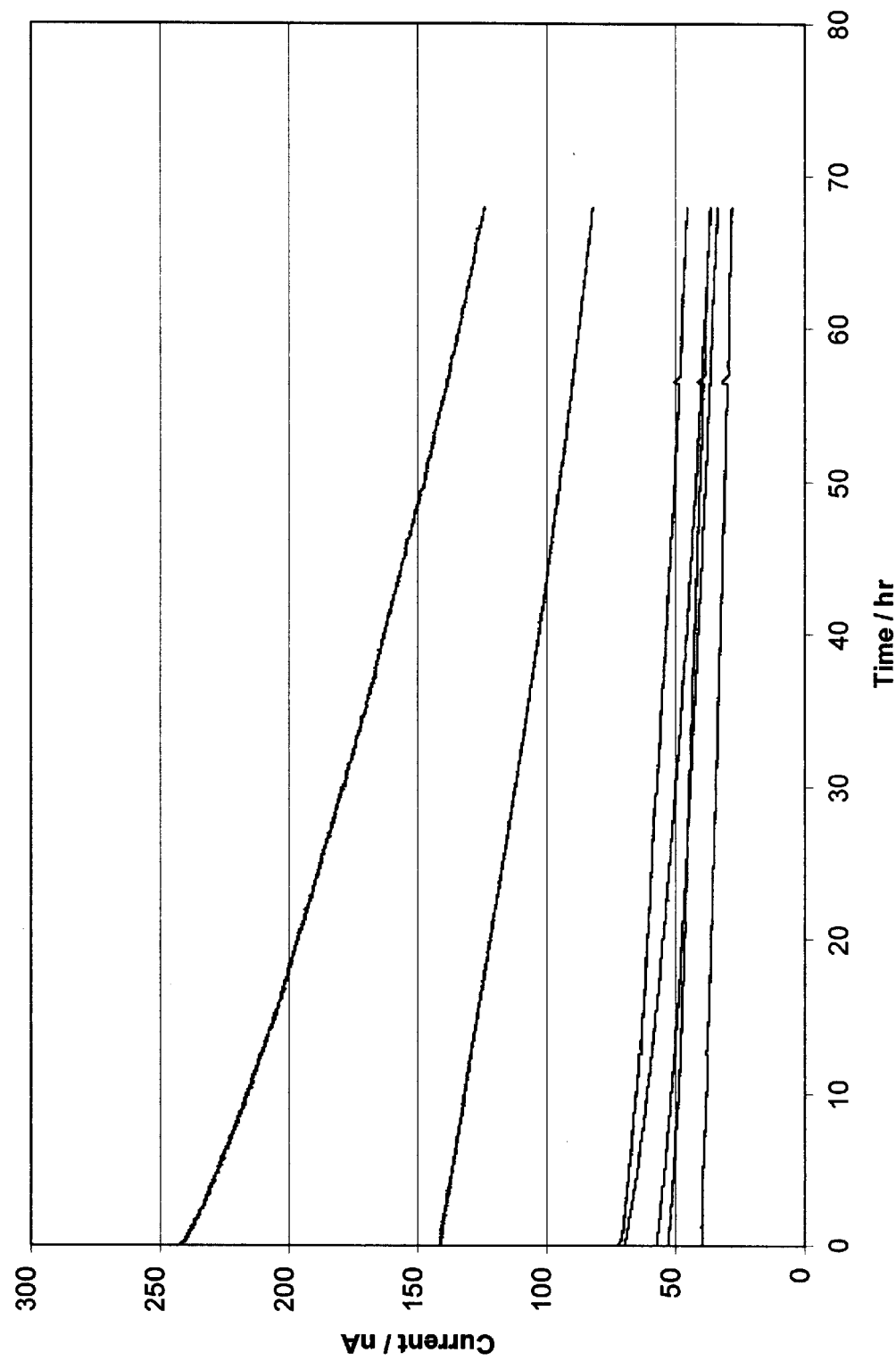
FIG. 15 shows a graph indicating the decline in signal of the sensors during the experiment of Examples 5.

The procedure from Example 2 was followed except that the sensing layer was composed of 24.3 wt. % X5, 28.8 wt. % glucose oxidase, 17.7 wt. % PEG-400-DGE, and 29.2 wt. % glycerol. Eight sensor were produced in accordance with this procedure, and tested. The results shown in FIGS. 13, 14, and 15 show acceptable current decline rates, and good sensitivity extending to high glucose concentrations. FIG. 13 shows the calibration curve for each of the sensors before the operation, FIG. 14 shows the calibration curve for each of the sensors after the operation, and FIG. 15 shows the decline in signal for each of the eight sensors during the operation.

We claim:

1. An electrochemical sensor for subcutaneous glucose sensing, the sensor comprising:
   a planar body having a top layer permeable to oxygen and impervious to glucose, a base layer impervious to glucose, and a peripheral edge;
   a working electrode disposed between the top layer and the base layer; and
   an analyte-responsive sensing layer proximate the working electrode, the sensing layer at least partially disposed between the working electrode and the top layer and extending to the peripheral edge of the sensor, so that contact with the glucose occurs only at the peripheral edge of the sensor, the sensing layer comprising glucose oxidase and a redox polymer.

2. The electrochemical sensor of claim 1, wherein the sensing layer further comprises a cross-linker.

3. The electrochemical sensor of claim 1, wherein the peripheral edge is a distal edge of the sensor.

4. The electrochemical sensor of claim 1, wherein the peripheral edge is a side edge of the sensor.

5. The electrochemical sensor of claim 1, wherein the sensor defines a channel having an inner peripheral surface extending into the sensor, and wherein the peripheral edge at which the sensing layer is exposed is defined by at least a portion of the inner peripheral surface of the channel.

6. The electrochemical sensor of claim 1, wherein the sensing layer is less than 100 µm thick.

7. The electrochemical sensor of claim 6, wherein the sensing layer is in the range of 1 to 10 µm thick.

8. The electrochemical sensor of claim 1, wherein the sensor body is flexible.

9. The electrochemical sensor of claim 1, wherein the sensing layer is non-leachably disposed on the sensor.

10. The electrochemical sensor of claim 1, wherein the sensor further includes a spacer layer at least partially disposed between the base layer and the top layer, the spacer layer defining a channel having an inner peripheral surface extending into the spacer layer, and wherein the peripheral edge at which the sensing layer is exposed is defined by at least a portion of the inner peripheral surface of the channel.

11. A method of determining the concentration of glucose in a body fluid of a mammal, the method comprising:

provided an electrochemical sensor comprising a planar body, a top layer permeable to oxygen and impervious to glucose, a base layer impervious to glucose, a working electrode between the top layer and the base layer, and an analyte-responsive sensing layer comprising glucose oxidase and redox polyer proximate the working electrode and between the working electrode and the top layer, the sensing layer exposed for contact with analyte only at a peripheral edge of the sensor;

implanting at least a portion of the sensor into the body of the mammal such that the edge of the sensor contacts body fluid of the mammal; and measuring the concentration of the glucose in body fluid of the mammal using the sensor.

12. The method of claim 11, wherein the peripheral edge is a distal edge of the sensor.

13. The method of claim 11, wherein the peripheral edge is a side edge of the sensor.

14. The method of claim 11, wherein the sensor defines a channel having an inner peripheral surface extending into the sensor, and wherein the peripheral edge at which the sensing layer is exposed is defined by at least a portion of the inner peripheral surface of the channel.

15. The method of claim 11, wherein the sensor further includes a spacer layer at least partially disposed between the base layer and the top layer, the spacer layer defining a channel having in inner peripheral surface extending into the spacer layer, and wherein the peripheral edge at which the sensing layer is exposed is defined by at least a portion of the inner peripheral surface of the channel.

16. The method of claim 11, wherein the sensor is subcutaneously implanted.

17. The method of claim 16, wherein the sensor is used to measure an analyte in subcutaneous fluid.

18. An electrochemical sensor for subcutaneous glucose sensing, the sensor comprising:

a planar body having a top layer permeable to oxygen and impervious to glucose, and a base layer impervious to glucose;

a working electrode disposed between the top layer and the base layer; and an analyte-responsive sensing layer comprising glucose oxidase and a redox polymer proximate the working electrode between the top layer and the working electrode, wherein the sensor defines a channel having therein an inner peripheral surface extending into the sensor, and wherein the sensing layer is exposed for contact with analyte only at a portion of the inner peripheral surface of the channel.

19. An electrochemical sensor for subcutaneous glucose sensing, the sensor comprising:

a planar sensor body having an outer portion impervious to glucose and at least a part of which is permeable to oxygen, and a peripheral edge;

a working electrode disposed within the sensor body; and an analyte-responsive sensing layer comprising glucose oxidase and redox polymer disposed at least partially between the outer portion and the working electrode and extending to the peripheral edge of the sensor for contact with glucose only at the edge of the sensor.

20. The electrochemical sensor of claim 19, wherein the exposed portion of the sensing layer is less than 100 μm thick.

21. The electrochemical sensor of claim 20, wherein the exposed portion of the sensing layer is in the range of 1 to 10 μm thick.

22. The electrochemical sensor of claim 19, wherein the sensor body further includes a spacer layer at least partially disposed between the base layer and the top layer, the spacer layer defining a channel having in inner peripheral surface extending into the spacer layer, and wherein the peripheral edge at which the sensing layer is exposed is defined by at least a portion of the inner peripheral surface of the channel.

23. The electrochemical sensor of claim 19, wherein the peripheral edge is a distal edge of the sensor body.

24. The electrochemical sensor of claim 19, wherein the peripheral edge is a side edge of the sensor body.

25. The electrochemical sensor of claim 19, wherein the sensor body defines a channel having an inner peripheral surface extending into the sensor body, and wherein the peripheral edge at which the sensing layer is exposed is defined by at least a portion of the inner peripheral surface of the channel.

* * * * *